(12) United States Patent
Zhang et al.

(10) Patent No.: US 9,176,112 B2
(45) Date of Patent: Nov. 3, 2015

(54) SYSTEMS AND METHODS FOR PLATELET COUNT WITH CLUMP ADJUSTMENT

(71) Applicant: Beckman Coulter, Inc., Brea, CA (US)

(72) Inventors: Shuliang Zhang, Miami, FL (US); Mark Rossman, Miami, FL (US); Jiuliu Lu, Homestead, FL (US); John Riley, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 14/145,608

(22) Filed: Dec. 31, 2013

(65) Prior Publication Data

US 2014/0185031 A1    Jul. 3, 2014

Related U.S. Application Data

(60) Provisional application No. 61/747,655, filed on Dec. 31, 2012.

(51) Int. Cl.

| | |
|---|---|
| *G01N 33/48* | (2006.01) |
| *G01N 33/49* | (2006.01) |
| *G01N 15/12* | (2006.01) |
| *G01N 15/10* | (2006.01) |
| *G01N 15/00* | (2006.01) |
| *G01N 15/14* | (2006.01) |

(52) U.S. Cl.
CPC ............ *G01N 33/49* (2013.01); *G01N 15/1031* (2013.01); *G01N 15/12* (2013.01); *G01N 15/1459* (2013.01); *G01N 2015/0084* (2013.01); *G01N 2015/1006* (2013.01); *G01N 2015/1037* (2013.01); *G01N 2015/1402* (2013.01); *G01N 2015/1486* (2013.01); *G01N 2015/1493* (2013.01)

(58) Field of Classification Search
CPC ............. G01N 2015/0076; G01N 2015/0084; G01N 2015/1413; G01N 35/1004; G01N 35/109; G01N 15/14; G01N 15/1404; G01N 1/14; G01N 2035/00356; G01N 2035/00524; G01N 2035/1032; G01N 35/0092; G01N 35/10

See application file for complete search history.

(56) References Cited

U.S. PATENT DOCUMENTS

| | | | |
|---|---|---|---|
| 6,025,201 | A | 2/2000 | Zelmanovic et al. |
| 6,133,995 | A | 10/2000 | Kubota |
| 2003/0096324 | A1 | 5/2003 | Matveev et al. |
| 2006/0160229 | A1 | 7/2006 | Lopez et al. |

(Continued)

FOREIGN PATENT DOCUMENTS

WO    9802727 A1    1/1998

OTHER PUBLICATIONS

Gill, et al.,"A Rapid and Accurate Closed-Tube Immunoassay for Platelets on an Automated Hematology Analyzer," Am. J. Clin. Pathol. 10 pages (2000).

(Continued)

*Primary Examiner* — Michael P Stafira
(74) *Attorney, Agent, or Firm* — Kilpatrick Townsend & Stockton LLP

(57) ABSTRACT

Embodiments of the present invention encompass automated systems and methods for analyzing platelet parameters in an individual based on a biological sample obtained from blood of the individual. Exemplary techniques involve correlating aspects of direct current (DC) impedance and/or light measurement data obtained from the biological sample with an evaluation of platelet conditions in the individual.

28 Claims, 20 Drawing Sheets

(56) References Cited

U.S. PATENT DOCUMENTS

| | | |
|---|---|---|
| 2007/0076190 A1 | 4/2007 | Nakaya et al. |
| 2007/0105230 A1 | 5/2007 | Perez et al. |
| 2007/0105231 A1 | 5/2007 | Riley et al. |
| 2007/0243523 A1 | 10/2007 | Ionescu-Zanetti et al. |
| 2009/0111118 A1 | 4/2009 | Mylvaganam et al. |
| 2009/0238439 A1 | 9/2009 | Wardlaw et al. |
| 2012/0262703 A1 | 10/2012 | Zahniser et al. |

OTHER PUBLICATIONS

Jones, et al., CELL-DYN 4000: Utility within the Core Laboratory Structure and Preliminary Comparison of its Expanded Differential with the 400-Cell Manual Differential Count, Laboratory Hematology, 11 pages (1998).

Matzdorff, et al., "Quantitative Assessment of Platelets, Platelet Microparticles, and Platelet Aggregates with Flow Cytometry," J Lab Clin Med. 11 pages (Jun. 1998).

Harrison, et al., "Immunoplatelet counting: a proposed new reference procedure," British Journal of Haematology, vol. 108, No. 2, Feb. 1, 2000, 8 pages.

International Search Report and Written Opinion of PCT/US2013/078543 mailed on Apr. 16, 2014, 16 pages.

Kubota, "Analysis of redcell and platelet morphology using an imaging-combined flow cytometer", Clinical & Laboratory Haematology, vol. 25, No. 2, Apr. 1, 2003, 6 pages.

"Laboratory 10 Manual Differential", www.austincc.edu/mlt/hem/hem_Lab_%20Manual%20Diff_F12.doc Jan. 1, 2012, point 3, p. 5.

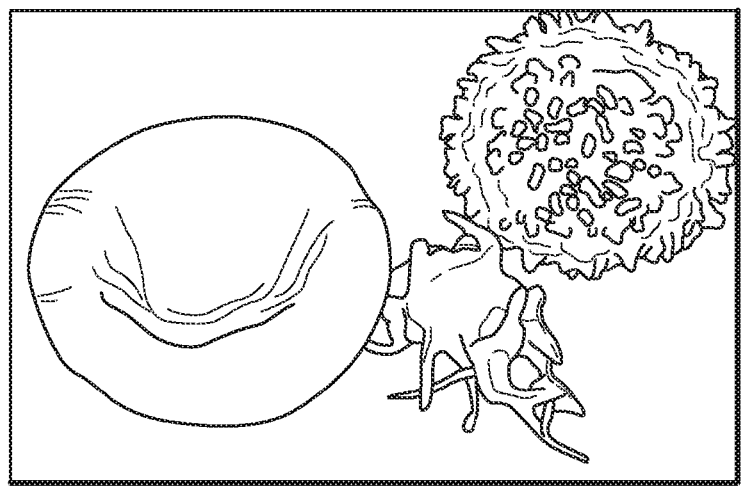
(RED BLOOD CELL, PLATELET, AND WHITE BLOOD CELL)
FIG.1A
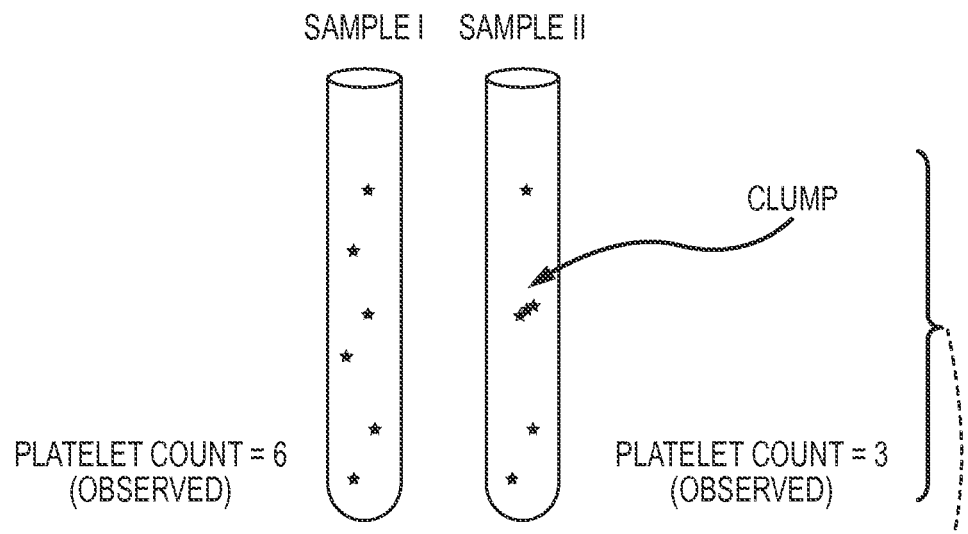
FIG.1B
PLATELET COUNT (CORRECTED)
=
PLATELET COUNT (OBSERVED) + PLATELET NUMBER CONTAINED IN CLUMPS
(ESTIMATED)
FIG.1C

FIG. 7

SYSTEMS AND METHODS FOR PLATELET COUNT WITH CLUMP ADJUSTMENT

CROSS-REFERENCES TO RELATED APPLICATIONS

This application is a non-provisional of and claims the benefit of the filing date of U.S. Provisional Application No. 61/747,655, filed on Dec. 31, 2012, which is herein incorporated by reference in its entirety for all purposes.

BACKGROUND OF THE INVENTION

This invention relates to the field of medical diagnostics and more specifically to systems and methods for enumerating platelets in a biological sample from a patient.

Platelets play an important physiological function in the body. For example, platelet activity is involved with blood clotting and wound repair. Various disease states can have an effect on the amount of platelets present within an individual's blood. Hence, a platelet count test can provide an important indication of a patient's health status. For example, platelet counts can be used to monitor or diagnose diseases that involve excessive bleeding or clotting.

On occasion, platelet clumps may form in a test sample vial before the sample is submitted to a platelet counting instrument for analysis. As a result, the platelet (PLT) count that is obtained may be artificially low. To address this issue, some current analyzers raise a flag to warn the user about a possible erroneous count as a result of clumping, and the users can then count the PLT with a manual slide review.

Hence, although platelet analysis systems and methods are currently available and provide real benefits to patients in need thereof, many advances may still be made to provide improved devices and methods for assessing the status of platelets in an individual. Embodiments of the present invention provide solutions that address these problems, and hence provide answers to at least some of these outstanding needs.

BRIEF SUMMARY OF THE INVENTION

Embodiments of the present invention provide improved techniques for analyzing platelet conditions or parameters in an individual. For example, certain embodiments encompass systems and methods for the correction of platelet count so as to account for the loss to platelet clumps. Such techniques can employ various combinations of Complete Blood Cell Count (CBC) parameters in addition to Volume Conductivity Scatter (VCS) parameters, so as to provide reliable screening approaches that assess platelet conditions of patients or individuals in the general population. For example, diagnostic systems and methods can provide an early and accurate prediction as to whether an individual has normal or abnormal platelet counts or parameters. Such platelet analysis techniques may involve directly calculating certain platelet measures, such as platelet count and platelet numbers contained in platelet clumps.

In certain embodiments, output obtained from CBC and NRBC modules can be combined to derive a platelet count that is compensated for platelet count events which may otherwise be lost due to the presence of platelet clumps. For example, a platelet count as reported by a CBC module (e.g. count of single unclumped platelets) can be combined with a lost platelet count (e.g. count of platelets occurring in clumps) that is estimated based on data from an NRBC module, so as to provide a corrected platelet count. Various techniques used to obtain a corrected platelet count may use different ways to calculate the number of platelets occurring in a single clump. For example, some methods may involve calculating the average number of platelets per clump. Other methods may involve calculating the most likely number of platelets in a clump for different clump sizes based on a probability distribution, and summing the entire clump size range to obtain the result.

Blood samples from patients who come under the care of a physician can be evaluated using a hematology system that is equipped to obtain multiple light angle detection parameters, such as a hematology analyzer. By employing the techniques disclosed herein, hematopathologists and clinicians can better predict disease prognosis for each individual patient, assess the likelihood of future complications, and quickly and accurately tailor the therapy offered to patients.

The hematology analyzer is able to directly recognize morphologic features indicative of types of blood components such as white blood cells, red blood cells, and platelets. As discussed elsewhere herein, this technology simultaneously collects data on various parameters that are directly correlated to cellular morphology or certain cellular events. As cellular components are analyzed, they can be plotted in histograms with their position being defined by various parameters. For example, since platelet clumps and other cellular particles may have different features, they can be plotted or segmented in different regions of the histogram, thus forming cell populations. The number of events in each population can be used to generate a count. Besides such counts, the mean and standard deviation values for the points of each of various morphologic parameters (volume, conductivity, and five angles of light scatter) can be calculated separately. As a result, a vast amount of data directly correlating to cellular events is generated. This information can be referred to as VCS data, and it can be viewed on the screen of the instrument, as well as automatically exported as an Excel file. Embodiments of the present invention may include evaluating a biological sample from an individual by obtaining a profile for the biological sample that involves VCS data, optionally in combination with CBC data, and assigning a platelet parameter such as an platelet count or platelet clump count to the biological sample based on the data. Certain embodiments may also include outputting a platelet related count indication. One or more of these steps may be performed by a hematology analyzer.

Embodiments of the present invention provide quick and accurate platelet screening results. Using the approaches disclosed herein, it is possible to evaluate and predict a platelet condition in an individual, using information obtained from a multiparametric cellular analysis system. As disclosed herein, exemplary cellular analysis systems can simultaneously measure parameters such as volume, conductivity, and/or multiple angles of light scatter. Such systems provide a high degree of resolution and sensitivity for implementing cellular analysis techniques. In some instances, cellular analysis systems detect light scatter at three, four, five, or more angular ranges. Additionally, cellular analysis systems also can detect signals at an angle between 0° to about 1° from the incident light, which corresponds to a light extinction parameter known as axial light loss. As a non-limiting example, a hematology analyzer provides light scatter detection data for multiple angles (e.g. between 0°-0.5° for AL2, about 5.1° for LALS, between 9°-19° for LMALS, and between 20°-43° for UMALS). These techniques allow for fast, accurate diagnosis and treatment of patients having abnormal platelet parameters, particularly in situations where more modern tests are not readily available.

Such hematology analysis instruments can evaluate more than 8,000 cells in a matter of seconds, and the morphologic features of cellular volume, cytoplasmic granularity, nuclear complexity, and internal density can be evaluated quantitatively. Numerical decision rules can be generated and used to implement strategies for predicting a platelet condition state or status in an individual. For example, a platelet condition state or status may be associated with a platelet count for the individual, optionally adjusted by an estimated count for platelets present in clumps. In some instances, the platelet condition or state may refer to a calculated platelet count or total platelet count (corrected) for the individual.

Hence, embodiments of the present invention encompass systems and methods for the diagnosis or monitoring of platelet associated conditions using multiparametric models for disease classification. Patterns of morphological change can be analyzed by combining information from various measured parameters. Hence, embodiments of the present invention are well suited for use in analyzing platelet parameters for evaluating disorders or conditions associated with lower than normal platelet counts (e.g. thrombocytopenia) such as disseminated intravascular coagulation (DIC), hemolytic anemia, hypersplenism, idiopathic thrombocytopenic purpura (ITP), leukemia, thrombotic thrombocytopenic purpura (TTP), celiac disease, and vitamin K deficiency, as well as disorders or conditions associated with higher than normal platelet counts (e.g. thrombocytosis) such as anemia, chronic myelogenous leukemia (CML), polycythemia vera, and primary thrombocythemia. Platelet analysis systems and methods as disclosed herein can also be used to provide indicators of marrow recovery in patients post-chemotherapy and stem cell transplant.

In one aspect, embodiments of the present invention encompass systems and methods for estimating a platelet status in an individual based on a biological sample obtained from blood of the individual. Exemplary systems include an optical element having a cell interrogation zone, a flow path configured to deliver a hydrodynamically focused stream of the biological sample toward the cell interrogation zone, an electrode assembly configured to measure direct current (DC) impedance of cells of the biological sample passing individually through the cell interrogation zone, a light source oriented to direct a light beam along a beam axis to irradiate the cells of the biological sample individually passing through the cell interrogation zone, and a light detection assembly optically coupled to the cell interrogation zone so as to measure light scattered by and transmitted through the irradiated cells of the biological sample. According to some embodiments, the light detection assembly is configured to measure a first propagated light from the irradiated cells within a first range of relative to the light beam axis, a second propagated light from the irradiated cells within a second range of angles relative to the light beam axis, where the second range is different than the first range, and an axial light propagated from the irradiated cells along the beam axis. In certain embodiments, the system is configured to correlate a subset of DC impedance, the first propagated light, the second propagated light, and the axial light measurements from the cells of the biological sample with an estimation of a platelet status in the individual. In some instances, the estimation of the platelet status in the individual includes a corrected platelet count based on an observed platelet count and a calculated lost clumped platelet count. The calculated lost clumped platelet count can be based on the subset of measurements, and the subset of measurements can be obtained via a nucleated red blood cell module. In some instances, the observed platelet count is based on data obtained from a complete blood cell count module. In some instances, the estimation of the platelet status in the individual includes an estimated platelet count based on an observed platelet count and a calculated lost clumped platelet count. In some instances, the DC measurement is obtained via a nucleated red blood cell module, and the system is configured to correlate the DC impedance measurement with the estimation of the platelet status of the individual. In some instances, the estimation of the platelet status in the individual includes an estimated platelet count based on an observed platelet count and a calculated lost clumped platelet count. The observed platelet count can be based on data obtained from a complete blood cell count module, and the calculated lost clumped platelet count can be based on data obtained from a nucleated red blood cell module. In some instances, the system includes the complete blood cell count module. In some instances, the DC impedance measurement is obtained via a nucleated red blood cell module, and the system is configured to correlate the DC impedance measurement with the estimation of the platelet status of the individual. In some instances, a light measurement of the subset is obtained via a nucleated red blood cell module, and the system is configured to correlate the light measurement obtained via the nucleated red blood cell module with the estimation of the platelet status of the individual. In some instances, a light measurement of the subset is obtained via a nucleated red blood cell module, the DC impedance measurement is obtained via a nucleated red blood cell module, and the system is configured to correlate the DC impedance measurement obtained via the nucleated red blood cell module, the light measurement obtained via the nucleated red blood cell module, and a platelet count obtained via a Complete Blood Cell Count module with the estimation of the platelet status of the individual, where the platelet status corresponds to a corrected platelet count. In some instances, the light measurement of the subset obtained via the nucleated red blood cell module includes a rotated lower angle light scatter (RLALS) measurement, an extended lower median angle light scatter (ELMALS) measurement, a rotated upper median angle light scatter (RUMALS) measurement, or an axial light loss (ALL) measurement. In some instances, the biological sample includes a blood sample of the individual.

In another aspect, embodiments of the present invention encompass systems and methods for estimating a platelet status in an individual based on a biological sample obtained from blood of the individual. Exemplary methods include delivering a hydrodynamically focused stream of the biological sample toward a cell interrogation zone of an optical element, measuring, with an electrode assembly, current (DC) impedance of cells of the biological sample passing individually through the cell interrogation zone, irradiating, with an electromagnetic beam having an axis, cells of the biological sample individually passing through the cell interrogation zone, measuring, with a light detection assembly, a first propagated light from the irradiated cells within a first range of relative to the beam axis, measuring, with the light detection assembly, a second propagated light from the irradiated cells within a second range of angles relative to the beam axis, the second range being different than the first range, measuring, with the light detection assembly, axial light propagated from the irradiated cells along the beam axis, and correlating a subset of DC impedance, the first propagated light, the second propagated light, and the axial light measurements from the cells of the biological sample with an estimated platelet status of the individual. In certain embodiments, the estimated platelet status in the individual includes a corrected platelet count based on an observed platelet count and a calculated lost clumped platelet count, where the calculated lost clumped platelet count is based on the subset of measurements, and where the subset of measurements is obtained via a nucleated red blood cell module.

In another aspect, embodiments of the present invention encompass systems and methods for evaluating a biological sample from an individual. Exemplary methods include obtaining a current light propagation data profile for the biological sample, assigning a platelet status indication to the biological sample based on the current light propagation data profile, and outputting the assigned platelet status indication. In certain embodiments, the platelet status indication includes a corrected platelet count based on an observed platelet count and a calculated lost clumped platelet count, where the calculated lost clumped platelet count is based on the current light propagation data profile, and where the current light propagation data profile is obtained via a nucleated red blood cell module.

In another aspect, embodiments of the present invention encompass automated systems and methods for estimating a platelet status of an individual based on a biological sample obtained from the individual. Exemplary systems include a conduit configured to receive and direct movement of the biological sample thorough an aperture, a light scatter and absorption measuring device configured to emit light through the biological sample as it moves through the aperture and collect data concerning scatter and absorption of the light, and a current measuring device configured to pass an electric current through the biological sample as it moves through the aperture and collect data concerning the electric current. In certain embodiments, the system is configured to correlate the data concerning scatter and absorption of the light and the data concerning the electric current with an estimated platelet status of the individual. In certain embodiments, the estimated platelet status of the individual includes a corrected platelet count based on an observed platelet count and a calculated lost clumped platelet count, where the calculated lost clumped platelet count is based on the data concerning scatter and absorption of the light and the data concerning the electric current, and where the data concerning scatter and absorption of the light and the data concerning the electric current is obtained via a nucleated red blood cell module.

In yet another aspect, embodiments of the present invention encompass automated systems and methods for estimating a platelet status of an individual based on a biological sample obtained from the individual. Exemplary systems include a storage medium, a processor, and a transducer for obtaining light scatter data, light absorption data, and current data for the biological sample as the sample passes through an aperture, a storage medium. The storage medium may include a computer application that, when executed by the processor, is configured to cause the system to use the light scatter data, the light absorption data, the current data, or a combination thereof, to determine an estimated platelet status of the individual, and to output from the processor information relating to the estimated platelet status. In certain embodiments, the estimated platelet status of the individual includes a corrected platelet count based on an observed platelet count and a calculated lost clumped platelet count, where the calculated lost clumped platelet count is based on the current data, and where the current data is obtained via a nucleated red blood cell module.

In still another aspect, embodiments of the present invention encompass automated systems and methods for estimating a platelet status of an individual based on a biological sample obtained from the individual. Exemplary systems include a storage medium, a processor, and a transducer for obtaining current light propagation data for the biological sample as the sample passes through an aperture. The storage medium may include a computer application that, when executed by the processor, is configured to cause the system to use the current light propagation data to determine an estimated platelet status of the individual, and to output from the processor information relating to the estimated platelet status.

In another aspect, embodiments of the present invention encompass systems and methods for identifying if an individual may have an abnormal platelet status based on a biological sample obtained from the individual. Exemplary systems include a storage medium, a processor, and a transducer for obtaining light scatter data, light absorption data, and current data for the biological sample as the sample passes through an aperture. In certain embodiments, the storage medium includes a computer application that, when executed by the processor, is configured to cause the system to use a parameter, which is based on one or more measures of the light scatter data, light absorption data, or current data, to determine an estimated platelet status of the individual, and to output from the processor platelet information relating to the estimated platelet status of the individual.

In still yet another aspect, embodiments of the present invention encompass systems and methods for evaluating a biological sample obtained from an individual. Exemplary methods include passing the biological sample through an aperture of a particle analysis system, obtaining light scatter data, light absorption data, and current data for the biological sample as the sample passes through the aperture, determining a current light propagation data profile for the biological sample based on the light scatter data, the light absorption data, the current data, or a combination thereof, assigning a platelet status indication to the biological sample based on the current light propagation data profile, and outputting the assigned platelet status indication.

In another aspect, embodiments of the present invention encompass automated systems and methods for evaluating a biological sample from an individual. Exemplary methods include obtaining, using a particle analysis system, light scatter data, light absorption data, and current data for the biological sample as the sample passes through an aperture, determining a current light propagation data profile for the biological sample based on assay results obtained from the particle analysis system, determining, using a computer system, an estimated platelet status for the individual according to a parameter, where the parameter is based on a current light propagation data measure of the current light propagation data profile, and outputting the estimated platelet status.

In another aspect, embodiments of the present invention encompass automated systems and methods for estimating a platelet status of an individual. Exemplary systems include a storage medium and a processor. The storage medium includes a computer application that, when executed by the processor, is configured to cause the system to access information concerning a biological sample of the individual, including information relating at least in part to an axial light loss measurement of the sample, a light scatter measurement of the sample, a current measurement of the sample, or a combination of two or more thereof, and to use the information relating at least in part to the axial light loss measurement, the plurality of light scatter measurements, the current measurement, or the combination thereof, to determine an estimated platelet status of the individual. The computer application may also, when executed by the processor, be configured to cause the system to output from the processor information relating to the estimated platelet status. In certain embodiments, the current measurement comprises a low frequency current measurement of the sample. In certain embodiments, the light scatter measurement includes a low angle light scatter measurement, a lower median angle light scatter measurement, an upper median angle light scatter measurement, or a combination of two or more thereof. In certain embodiments, a system may include an electromagnetic beam source and a photosensor assembly, where the photosensor assembly is used to obtain the axial light loss measurement. In certain embodiments, a system may include an electromagnetic beam source and a photosensor assembly, where the photosensor assembly is used to obtain the light scatter measurement. In certain embodiments, a system may include an electromagnetic beam source and an electrode assembly, where the electrode assembly is used to obtain the current measurement.

In still another aspect, embodiments of the present invention encompass automated systems and methods for estimating a platelet status of an individual. Exemplary systems include a storage medium and a processor. A storage medium may include a computer application that, when executed by the processor, is configured to cause the system to access current light propagation data concerning a biological sample of the individual, to use the current light propagation data to determine an estimated platelet status of the individual, and to output from the processor information relating to the estimated platelet status. In certain embodiments, the processor is configured to receive the current light propagation data as input. In certain embodiments, the processor, the storage medium, or both, are incorporated within a hematology machine. In certain embodiments, the hematology machine generates the current light propagation data. In certain embodiments, the processor, the storage medium, or both, are incorporated within a computer, and the computer is in communication with a hematology machine. In certain embodiments, the hematology machine generates the current light propagation. In certain embodiments, the processor, the storage medium, or both, are incorporated within a computer, and the computer is in remote communication with a hematology machine via a network. In certain embodiments, the hematology machine generates the current light propagation data. In certain embodiments, the current light propagation data includes an axial light loss measurement of the sample, a light scatter measurement of the sample, a current measurement of the sample, or a combination thereof.

In another aspect, embodiments of the present invention encompass automated systems and methods for evaluating the physiological status of an individual. Exemplary systems include a storage medium and a processor. The storage medium may include a computer application that, when executed by the processor, is configured to cause the system to access current light propagation data concerning a biological sample of the individual, and to use a parameter, which is based on a measure of the current light propagation data, to determine the physiological status of the individual, where the determined physiological status provides an indication whether the individual has a normal platelet status. The computer application may also, when executed by the processor, be configured to cause the system to output from the processor information relating to the physiological status of the individual.

In a further aspect, embodiments of the present invention encompass systems and methods for identifying if an individual may have an abnormal platelet status from hematology system data. Exemplary systems include a storage medium and a processor. The storage medium may include a computer application that, when executed by the processor, is configured to cause the system to access hematology current light propagation data concerning a blood sample of the individual, and to use a parameter, which is based on a measure of the hematology current light propagation data, to determine an estimated platelet status of the individual. The computer application may also, when executed by the processor, be configured to cause the system to output from the processor platelet information relating to the estimated platelet status of the individual.

In another aspect, embodiments of the present invention encompass automated systems and methods for evaluating a biological sample from an individual. Exemplary methods include determining a current light propagation data profile for the biological sample based on assay results obtained from a particle analysis system analyzing the sample, and determining, using a computer system, a physiological status for the individual according to a parameter, where the parameter is based on a function of a current light propagation data measure of the current light propagation data profile, and where the physiological status provides an indication whether the individual has a normal platelet status. Methods may also include outputting the physiological status.

In still yet another aspect, embodiments of the present invention encompass systems and methods for determining a treatment regimen for a patient. Exemplary methods include accessing a current light propagation data profile concerning a biological sample of the patient, and determining, using a computer system, an estimated platelet status for the patient based on the current light propagation data profile. Methods may also include determining the treatment regimen for the patient based on the estimated platelet status. Some methods may include administering the treatment regimen to the patient. In certain embodiments, the estimated platelet status may include a positive indication for a platelet-related disease.

In still yet a further aspect, embodiments of the present invention encompass systems and methods for determining a treatment regimen for an individual Exemplary methods may include accessing a current light propagation data profile concerning a biological sample of the individual, and determining, using a computer system, a physiological status for the individual according to a parameter, where the parameter is based on a current light propagation data measure of the current light propagation data profile, and where the physiological status corresponds to an estimated platelet status. Exemplary methods may also include determining the treatment regimen for the individual based on the a physiological status for the individual.

In another aspect, embodiments of the present invention encompass automated systems and methods for estimating a platelet status of an individual based on a biological sample obtained from blood of the individual. Exemplary systems may include an optical element having a cell interrogation zone, a flow path configured to deliver a hydrodynamically focused stream of the biological sample toward the cell interrogation zone, an electrode assembly configured to measure direct current (DC) impedance of cells of the biological sample passing individually through the cell interrogation zone, a light source oriented to direct a light beam along a beam axis to irradiate the cells of the biological sample individually passing through the cell interrogation zone, and a light detection assembly optically coupled to the cell interrogation zone. In certain embodiments, the light detection assembly may include a first sensor region disposed at a first location relative to the cell interrogation zone that detects a first propagated light, a second sensor region disposed at a second location relative to the cell interrogation zone that detects a second propagated light, and a third sensor region disposed at a third location relative to the cell interrogation zone that detects an axial propagated light. In certain embodiments, the system is configured to correlate a subset of DC impedance, the first propagated light, the second propagated light, and the axial light measurements from the cells of the biological sample with an estimated platelet status of the individual.

In still another aspect, embodiments of the present invention encompass automated systems and methods for estimating a platelet status in an individual based on a biological sample obtained from blood of the individual. Exemplary systems include an optical element having a cell interrogation zone, a flow path configured to deliver a hydrodynamically focused stream of the biological sample toward the cell interrogation zone, an electrode assembly configured to measure direct current (DC) impedance of cells of the biological sample passing individually through the cell interrogation zone, a light source oriented to direct a light beam along a beam axis to irradiate the cells of the biological sample individually passing through the cell interrogation zone, and a light detection assembly optically coupled to the cell interrogation zone so as to measure light scattered by and transmitted through the irradiated cells of the biological sample. The light detection assembly can be configured to measure a first propagated light from the irradiated cells within a first range of relative to the light beam axis, a second propagated light from the irradiated cells within a second range of angles relative to the light beam axis, the second range being different than the first range, and an axial light propagated from the irradiated cells along the beam axis. In certain embodiments, the system is configured to correlate a subset of Complete Blood Cell Count platelet measurements from the cells of the biological sample combined with the subset of DC impedance, the first propagated light, the second propagated light, and the axial light measurements with the estimation of the platelet status in the individual. In some cases, the light detection assembly includes a first sensor zone that measures the first propagated light, a second sensor zone that measures the second propagated light, and a third sensor zone that measures the axial propagated light. In some cases, the light detection assembly includes a first sensor that measures the first propagated light, a second sensor that measures the second propagated light, and a third sensor that measures the axial propagated light. In some cases, the system is configured to correlate a subset of Complete Blood Cell Count measurements from the cells of the biological sample combined with the subset of DC impedance, the first propagated light, the second propagated light, and the axial light measurements with the estimation of the platelet status in the individual. In some cases, the biological sample is a blood sample of the individual.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIGS. 1A to 1C illustrate aspects of platelet counting and analysis, according to embodiments of the present invention.

FIG. 7 depicts an exemplary screen shot of a count analysis technique, according to embodiments of the present invention.

DETAILED DESCRIPTION OF THE INVENTION

Figure 2:
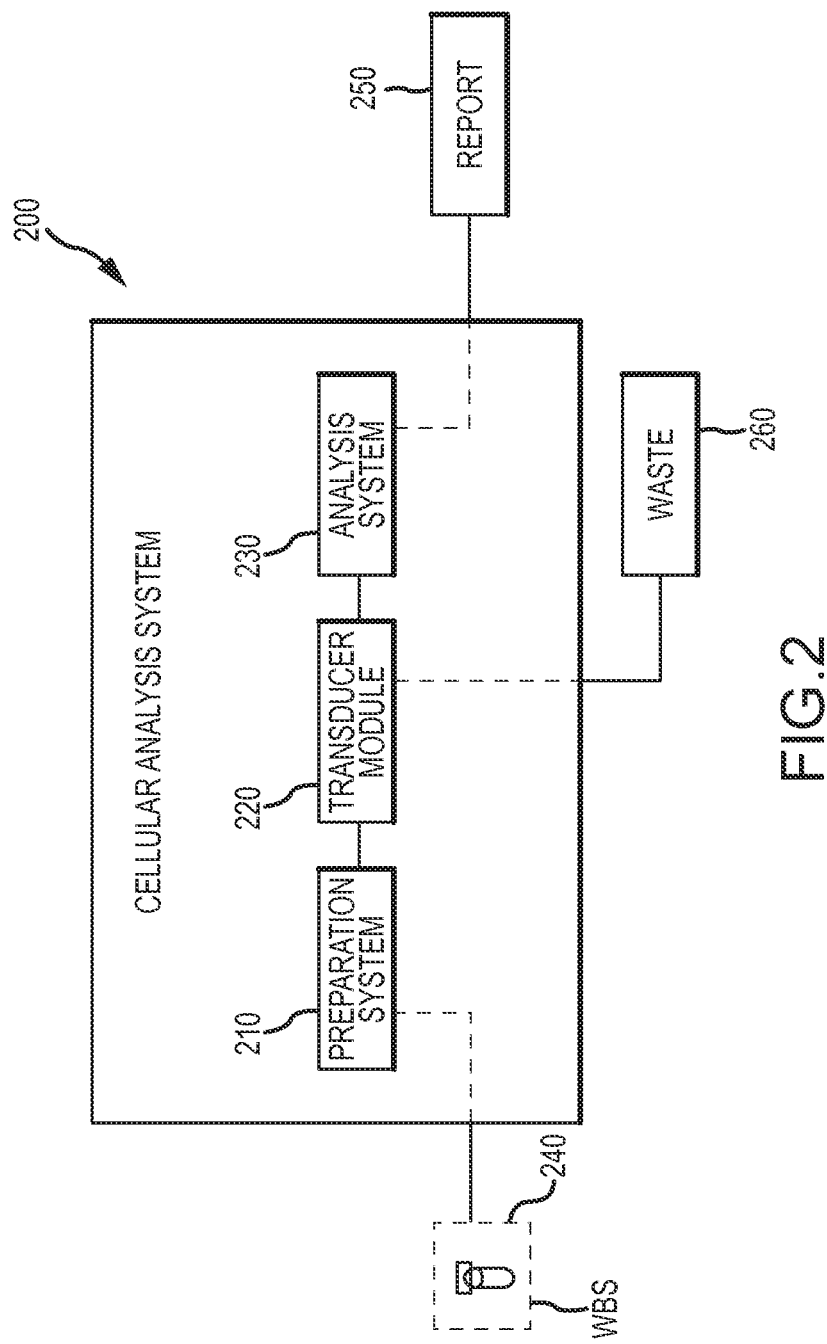
FIG. 2 schematically depicts aspects of a cellular analysis system, according to embodiments of the present invention.

For the purposes of explanation, and in brief overview, embodiments of the present invention encompass systems and methods which involve the use a nucleated red blood cell (NRBC) module in a hematological analyzer for obtaining platelet counts corrected for platelet clumping. An exemplary hematological cell analyzer may include a light source that produces a narrow directed beam of light toward a window in a flow cell. In various non-limiting embodiments, the light source is a laser or a laser diode, and a carrier fluid carries individual cells from a blood sample through the flow cell thereby allowing each individual cell to interact with the light beam. A plurality of photosensors located adjacent the flow cell can be used to record the intensity of light scattered at various angles by cells passing through the flow cell. In certain embodiments, one photosensor is positioned directly in the path of the light beam, and three groups of photosensors are positioned to collect light scattered by the cells in predetermined angular ranges as measured from the path of the light beam. Signals from these detectors can be transmitted to a processor, digitized, analyzed and the results displayed.

According to some embodiments, an NRBC module can be used to analyze blood cells of a biological sample obtained from an individual. Certain NRBC processing techniques involve diluting a portion of a whole blood sample and treating the dilution with a lysing reagent that selectively removes non-nucleated red blood cells while maintaining the maintains the integrity of NRBCs, WBCs, and any platelets or cellular debris that may be present. Exemplary NRBC processing techniques are also discussed in U.S. Pat. No. 7,208,319, the content of which is incorporated herein by reference.

Hence, described herein are hematology systems and methods configured to assess platelet status conditions of an individual, based on a biological sample obtained from the individual. FIG. 1A provides a scanning electron micrograph of blood cells, including a red blood cell (left, human erythrocyte), platelet (middle, thrombocyte), and white blood cell (right, leukocyte). Each of these three blood cell types are generated in the bone marrow. Platelets are derived from megakaryocytes, which are large cells in the bone marrow.

Megakaryocytes extend into small vessels of the bone marrow, and fragments of the megakaryocyte cytoplasm are released to form immature platelets. The platelets mature following release into the blood circulation. Platelets have a life cycle of about 7-10 days, and platelet formation and replacement is a continuous cycle. Platelets play an important role in hemostasis and clot formation.

FIG. 1B provides a schematic illustration of how may clumps may or may not be present in a biological sample. For instance, Sample I contains no platelet clumps, whereas platelet clumping is present in Sample II. As shown here, clump artifacts in platelet measurements may be lost when analyzing blood with an automated system (e.g. only unclumped platelets are detected as such by the machine), thus providing an inaccurate count, or requiring time consuming manual measurements to obtain the true platelet count.

As depicted in FIG. 1C, various platelet parameters can be evaluated to assess the platelet status of an individual. For example, exemplary evaluation techniques may involve obtaining a observed count of platelets in the blood, as well as an estimated number of platelets contained in clumps within the sample. Hence, embodiments of the present invention encompass systems and methods for enumerating and differentiating platelets in a blood sample using a particle analyzer. Certain analysis techniques can be used to estimate a corrected platelet count by estimating platelet numbers contained in platelet clumps, and then adding this estimated value to the actual number of platelets counted in order to arrive at a total platelet count (corrected). Relatedly, the hematology systems and methods discussed herein can assess whether an individual is presenting with normal or abnormal platelet parameters based on data related to certain impedance, conductivity, and angular light propagation measurements of a biological sample of the individual.

Cellular analysis systems that detect light scatter at multiple angles can be used to analyze a biological sample (e.g. a blood sample) and output a predicted platelet status of an individual. Exemplary systems are equipped with sensor assemblies that obtain light scatter data for three or more angular ranges, in addition to light transmission data associated with an extinction or axial light loss measure, and thus provide accurate, sensitive, and high resolution results without requiring the use of certain dye, antibody, or fluorescence techniques. In one instance, a hematology analyzer is configured to analyze a biological sample (e.g. a blood sample) based on multiple light scatter angles and output a predicted platelet status of an individual. The hematology analyzer includes various channel processing modules that are configured to recognize the morphologic features indicative of cellular components within the blood. For example, the hematology analyzer includes a NRBC channel processing module that is configured to analyze certain blood cell components. The hematology analyzer is configured to generate a significant amount of data based on analysis of the sample, this such data, which is described in detail herein, can be referred to as CBC data or VCS data.

In some embodiments, VCS data is based on the determination of different parameters for each cell of the sample analyzed, such parameters correlating to each cell's morphology. Specifically, a volume parameter corresponding to the cell size can be measured directly by impedance. Further, a conductivity parameter corresponding to the internal cellular density can be measured directly by the conduction of radio frequency waves across the cell. What is more, five different angles (or ranges of angles) of light scatter corresponding to cytoplasmic granularity and nuclear complexity, for example, can be measured with various light detection mechanisms.

FIG. 2 schematically depicts a cellular analysis system 200. As shown here, system 200 includes a preparation system 210, a transducer module 220, and an analysis system 230. While system 200 is herein described at a very high level, with reference to the three core system blocks (210, 220, and 230), the skilled artisan would readily understand that system 200 includes many other system components such as central control processor(s), display system(s), fluidic system(s), temperature control system(s), user-safety control system(s), and the like. In operation, a whole blood sample (WBS) 240 can be presented to the system 200 for analysis. In some instances, WBS 240 is aspirated into system 200. Exemplary aspiration techniques are known to the skilled artisan. After aspiration, WBS 240 can be delivered to a preparation system 210. Preparation system 210 receives WBS 240 and can perform operations involved with preparing WBS 240 for further measurement and analysis. For example, preparation system 210 may separate WBS 240 into predefined aliquots for presentation to transducer module 220. Preparation system 210 may also include mixing chambers so that appropriate reagents may be added to the aliquots. For example, where an aliquot is to be tested for differentiation of white blood cell subset populations, a lysing reagent (e.g. ERYTHROLYSE, a red blood cell lysing buffer) may be added to the aliquot to break up and remove the RBCs. Preparation system 210 may also include temperature control components to control the temperature of the reagents and/or mixing chambers. Appropriate temperature controls can improve the consistency of the operations of preparation system 210.

In some instances, predefined aliquots can be transferred from preparation system 210 to transducer module 220. As described in further detail below, transducer module 220 can perform direct current (DC) impedance, radiofrequency (RF) conductivity, light transmission, and/or light scatter measurements of cells from the WBS passing individually therethrough. Measured DC impedance, RF conductivity, and light propagation (e.g. light transmission, light scatter) parameters can be provided or transmitted to analysis system 230 for data processing. In some instances, analysis system 230 may include computer processing features and/or one or more modules or components such as those described herein with reference to the system depicted in FIG. 6 and described further below, which can evaluate the measured parameters, identify and enumerate the blood cellular constituents, and correlate a subset of data characterizing elements of the WBS with a platelet status of the individual. As shown here, cellular analysis system 200 may generate or output a report 250 containing the predicted platelet status and/or a prescribed treatment regimen for the individual. In some instances, excess biological sample from transducer module 220 can be directed to an external (or alternatively internal) waste system 260.

Treatment regimens may involve administration of one or more medications or therapeutic agents to an individual for the purposes of addressing the patient's condition. Any of a variety of therapeutic modalities can be used for treating an individual identified as having an abnormal platelet count as discussed herein.

Figure 3:
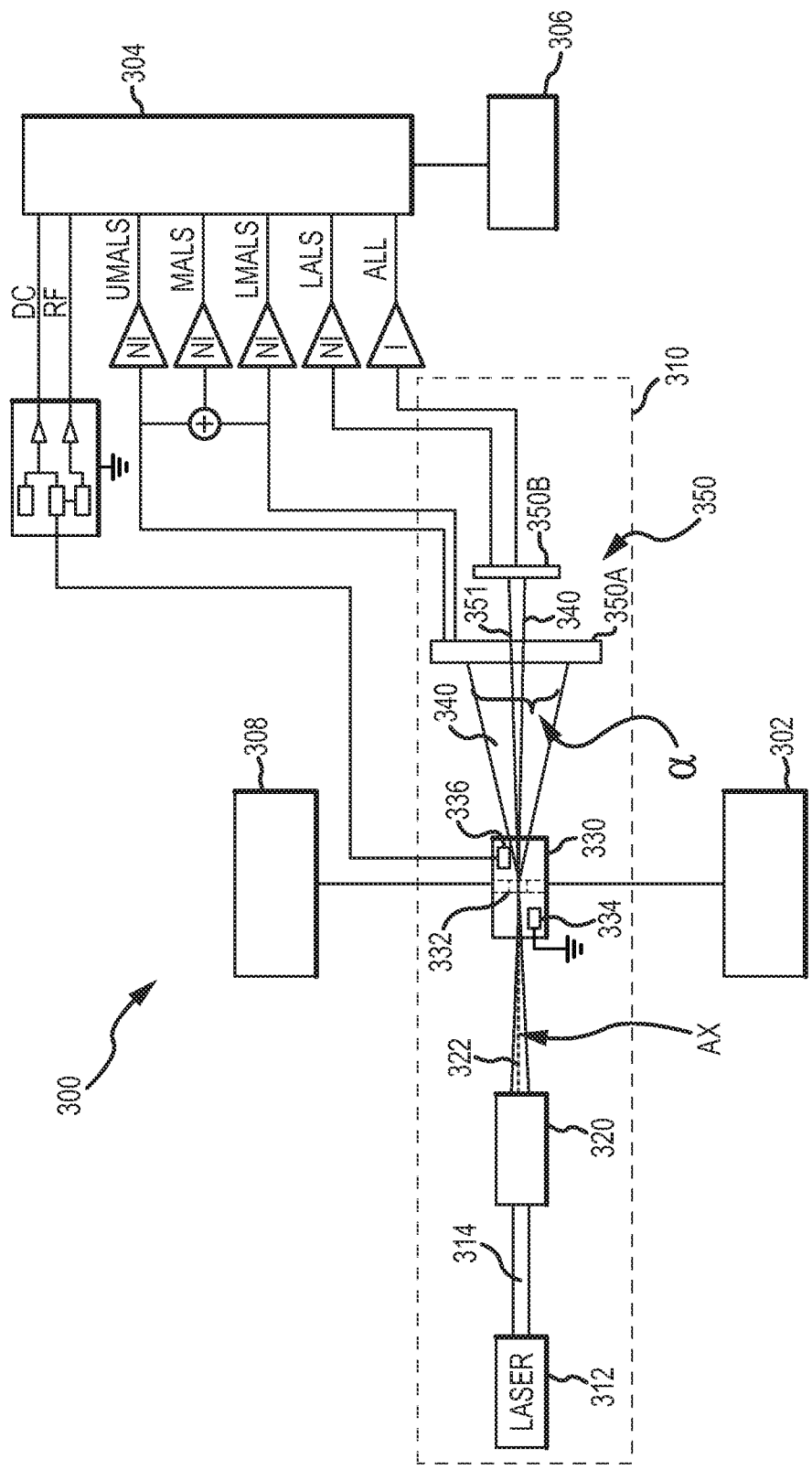
FIG. 3 provides a system block diagram illustrating aspects of a cellular analysis system according to embodiments of the present invention.

FIG. 3 illustrates in more detail a transducer module and associated components in more detail. As shown here, system 300 includes a transducer module 310 having a light or irradiation source such as a laser 310 emitting a beam 314. The laser 312 can be, for example, a 635 nm, 5 mW, solid-state laser. In some instances, system 300 may include a focus-alignment system 320 that adjusts beam 314 such that a resulting beam 322 is focused and positioned at a cell interrogation zone 332 of a flow cell 330. In some instances, flow cell 330 receives a sample aliquot from a preparation system 302. As described elsewhere herein, various fluidic mechanisms and techniques can be employed for hydrodynamic focusing of the sample aliquot within flow cell 330.

In some instances, the aliquot generally flows through the cell interrogation zone 332 such that its constituents pass through the cell interrogation zone 332 one at a time. In some cases, a system 300 may include a cell interrogation zone or other feature of a transducer module or blood analysis instrument such as those described in U.S. Pat. Nos. 5,125,737; 6,228,652; 7,390,662; 8,094,299; and 8,189,187, the contents of which are incorporated herein by references. For example, a cell interrogation zone 332 may be defined by a square transverse cross-section measuring approximately 50×50 microns, and having a length (measured in the direction of flow) of approximately 65 microns. Flow cell 330 may include an electrode assembly having first and second electrodes 334, 336 for performing DC impedance and RF conductivity measurements of the cells passing through cell interrogation zone 332. Signals from electrodes 334, 336 can be transmitted to analysis system 304. The electrode assembly can analyze volume and conductivity characteristics of the cells using low-frequency current and high-frequency current, respectively. For example, low-frequency DC impedance measurements can be used to analyze the volume of each individual cell passing through the cell interrogation zone. Relatedly, high-frequency RF current measurements can be used to determine the conductivity of cells passing through the cell interrogation zone. Because cell walls act as conductors to high frequency current, the high frequency current can be used to detect differences in the insulating properties of the cell components, as the current passes through the cell walls and through each cell interior. High frequency current can be used to characterize nuclear and granular constituents and the chemical composition of the cell interior.

Incoming beam 322 travels along beam axis AX and irradiates the cells passing through cell interrogation zone 332, resulting in light propagation within an angular range α (e.g. scatter, transmission) emanating from the zone 332. Exemplary systems are equipped with sensor assemblies that can detect light within three, four, five, or more angular ranges within the angular range α, including light associated with an extinction or axial light loss measure as described elsewhere herein. As shown here, light propagation 340 can be detected by a light detection assembly 350, optionally having a light scatter detector unit 350A and a light scatter and transmission detector unit 350B. In some instances, light scatter detector unit 350A includes a photoactive region or sensor zone for detecting and measuring upper median angle light scatter (UMALS), for example light that is scattered or otherwise propagated at angles relative to a light beam axis within a range from about 20 to about 42 degrees. In some instances, UMALS corresponds to light propagated within an angular range from between about 20 to about 43 degrees, relative to the incoming beam axis which irradiates cells flowing through the interrogation zone. Light scatter detector unit 350A may also include a photoactive region or sensor zone for detecting and measuring lower median angle light scatter (LMALS), for example light that is scattered or otherwise propagated at angles relative to a light beam axis within a range from about 10 to about 20 degrees. In some instances, LMALS corresponds to light propagated within an angular range from between about 9 to about 19 degrees, relative to the incoming beam axis which irradiates cells flowing through the interrogation zone.

A combination of UMALS and LMALS is defined as median angle light scatter (MALS), which is light scatter or propagation at angles between about 9 degrees and about 43 degrees relative to the incoming beam axis which irradiates cells flowing through the interrogation zone.

As shown in FIG. 3, the light scatter detector unit 350A may include an opening 351 that allows low angle light scatter or propagation 340 to pass beyond light scatter detector unit 350A and thereby reach and be detected by light scatter and transmission detector unit 350B. According to some embodiments, light scatter and transmission detector unit 350B may include a photoactive region or sensor zone for detecting and measuring lower angle light scatter (LALS), for example light that is scattered or propagated at angles relative to an irradiating light beam axis of about 5.1 degrees. In some instances, LALS corresponds to light propagated at an angle of less than about 9 degrees, relative to the incoming beam axis which irradiates cells flowing through the interrogation zone. In some instances, LALS corresponds to light propagated at an angle of less than about 10 degrees, relative to the incoming beam axis which irradiates cells flowing through the interrogation zone. In some instances, LALS corresponds to light propagated at an angle of about 1.9 degrees±0.5 degrees, relative to the incoming beam axis which irradiates cells flowing through the interrogation zone. In some instances, LALS corresponds to light propagated at an angle of about 3.0 degrees±0.5 degrees, relative to the incoming beam axis which irradiates cells flowing through the interrogation zone. In some instances, LALS corresponds to light propagated at an angle of about 3.7 degrees±0.5 degrees, relative to the incoming beam axis which irradiates cells flowing through the interrogation zone. In some instances, LALS corresponds to light propagated at an angle of about 5.1 degrees±0.5 degrees, relative to the incoming beam axis which irradiates cells flowing through the interrogation zone. In some instances, LALS corresponds to light propagated at an angle of about 7.0 degrees±0.5 degrees, relative to the incoming beam axis which irradiates cells flowing through the interrogation zone.

According to some embodiments, light scatter and transmission detector unit 350B may include a photoactive region or sensor zone for detecting and measuring light transmitted axially through the cells, or propagated from the irradiated cells, at an angle of 0 degrees relative to the incoming light beam axis. In some cases, the photoactive region or sensor zone may detect and measure light propagated axially from cells at angles of less than about 1 degree relative to the incoming light beam axis. In some cases, the photoactive region or sensor zone may detect and measure light propagated axially from cells at angles of less than about 0.5 degrees relative to the incoming light beam axis less. Such axially transmitted or propagated light measurements correspond to axial light loss (ALL or AL2). As noted in previously incorporated U.S. Pat. No. 7,390,662, when light interacts with a particle, some of the incident light changes direction through the scattering process (i.e. light scatter) and part of the light is absorbed by the particles. Both of these processes remove energy from the incident beam. When viewed along the incident axis of the beam, the light loss can be referred to as forward extinction or axial light loss. Additional aspects of axial light loss measurement techniques are described in U.S. Pat. No. 7,390,662 at column 5, line 58 to column 6, line 4.

As such, the cellular analysis system 300 provides means for obtaining light propagation measurements, including light scatter and/or light transmission, for light emanating from the irradiated cells of the biological sample at any of a variety of angles or within any of a variety of angular ranges, including ALL and multiple distinct light scatter or propagation angles. For example, light detection assembly 350, including appropriate circuitry and/or processing units, provides a means for detecting and measuring UMALS, LMALS, LALS, MALS, and ALL.

Wires or other transmission or connectivity mechanisms can transmit signals from the electrode assembly (e.g. electrodes 334, 336), light scatter detector unit 350A, and/or light scatter and transmission detector unit 350B to analysis system 304 for processing. For example, measured DC impedance, RF conductivity, light transmission, and/or light scatter parameters can be provided or transmitted to analysis system 304 for data processing. In some instances, analysis system 304 may include computer processing features and/or one or more modules or components such as those described herein with reference to the system depicted in FIG. 6, which can evaluate the measured parameters, identify and enumerate biological sample constituents, and correlate a subset of data characterizing elements of the biological sample with a platelet status of the individual. As shown here, cellular analysis system 300 may generate or output a report 306 containing the predicted platelet status and/or a prescribed treatment regimen for the individual. In some instances, excess biological sample from transducer module 310 can be directed to an external (or alternatively internal) waste system 308. In some instances, a cellular analysis system 300 may include one or more features of a transducer module or blood analysis instrument such as those described in previously incorporated U.S. Pat. Nos. 5,125,737; 6,228,652; 8,094,299; and 8,189,187.

Figure 4:
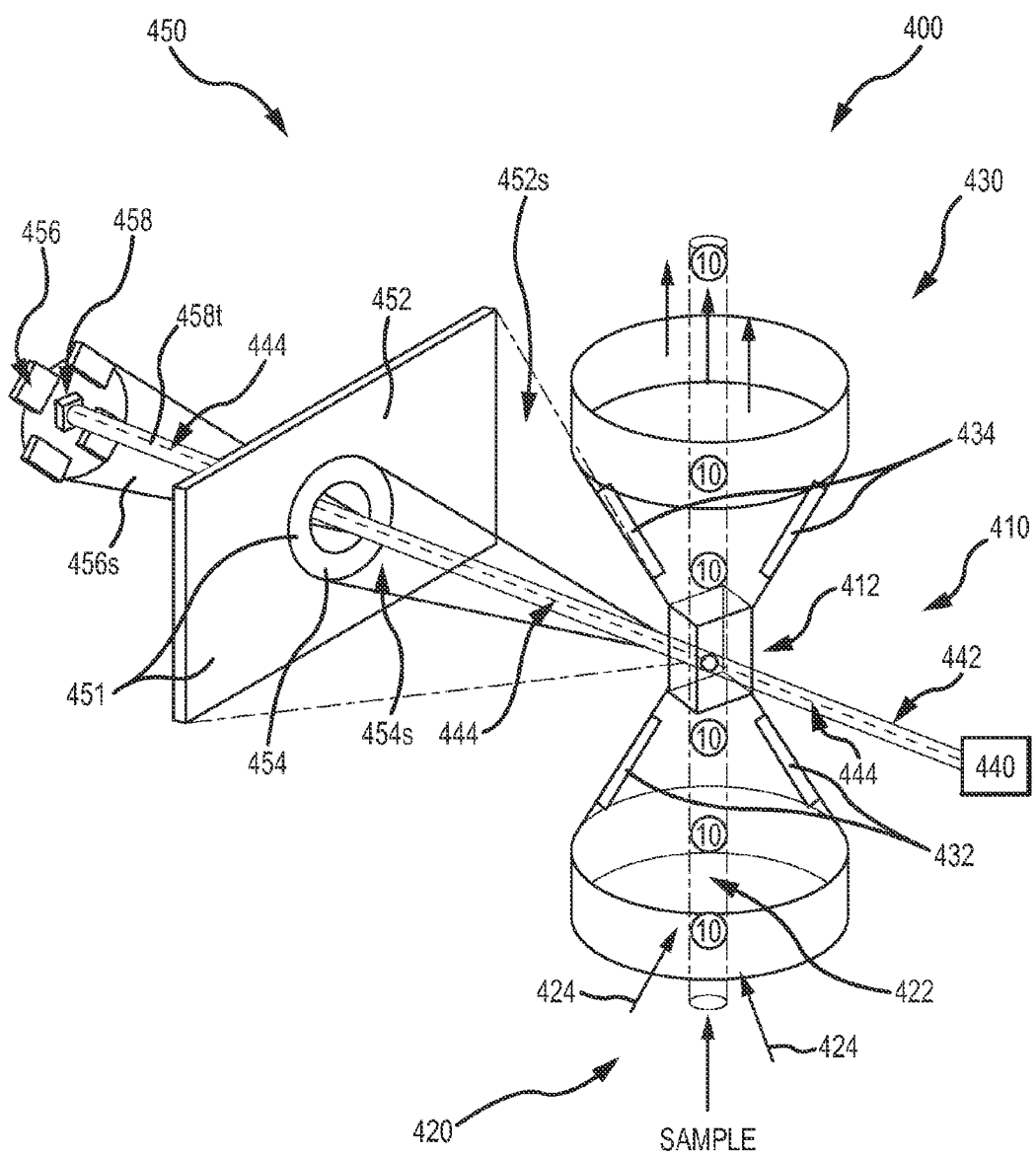
FIG. 4 illustrates aspects of an automated cellular analysis system for evaluating the platelet status of an individual, according to embodiments of the present invention.

FIG. 4 illustrates aspects of an automated cellular analysis system for predicting or assessing a platelet status of an individual, according to embodiments of the present invention. In particular, the platelet status can be predicted based on a biological sample obtained from blood of the individual. As shown here, an analysis system or transducer 400 may include an optical element 410 having a cell interrogation zone 412. The transducer also provides a flow path 420, which delivers a hydrodynamically focused stream 422 of a biological sample toward the cell interrogation zone 412. For example, as the sample stream 422 is projected toward the cell interrogation zone 412, a volume of sheath fluid 424 can also enter the optical element 410 under pressure, so as to uniformly surround the sample stream 422 and cause the sample stream 422 to flow through the center of the cell interrogation zone 412, thus achieving hydrodynamic focusing of the sample stream. In this way, individual cells of the biological sample, passing through the cell interrogation zone one cell at a time, can be precisely analyzed.

Transducer module or system 400 also includes an electrode assembly 430 that measures direct current (DC) impedance and radiofrequency (RF) conductivity of cells 10 of the biological sample passing individually through the cell interrogation zone 412. The electrode assembly 430 may include a first electrode mechanism 432 and a second electrode mechanism 434. As discussed elsewhere herein, low-frequency DC measurements can be used to analyze the volume of each individual cell passing through the cell interrogation zone. Relatedly, high-frequency RF current measurements can be used to determine the conductivity of cells passing through the cell interrogation zone. Such conductivity measurements can provide information regarding the internal cellular content of the cells. For example, high frequency RF current can be used to analyze nuclear and granular constituents, as well as the chemical composition of the cell interior, of individual cells passing through the cell interrogation zone.

The system 400 also includes a light source 440 oriented to direct a light beam 442 along a beam axis 444 to irradiate the cells 10 of the biological sample individually passing through the cell interrogation zone 412. Relatedly, the system 400 includes a light detection assembly 450 optically coupled with the cell interrogation zone, so as to measure light scattered by and transmitted through the irradiated cells 10 of the biological sample. The light detection assembly 450 can include a plurality of light sensor zones that detect and measure light propagating from the cell interrogation zone 412. In some instances, the light detection assembly detects light propagated from the cell interrogation zone at various angles or angular ranges relative to the irradiating beam axis. For example, light detection assembly 450 can detect and measure light that is scattered at various angles by the cells, as well as light that is transmitted axially by the cells along the beam axis. The light detection assembly 450 can include a first sensor zone 452 that measures a first scattered or propagated light 452$s$ within a first range of angles relative to the light beam axis 444. The light detection assembly 450 can also include a second sensor zone 454 that measures a second scattered or propagated light 454$s$ within a second range of angles relative to the light beam axis 444. As shown here, the second range of angles for scattered or propagated light 454$s$ is different from the first range of angles for scattered or propagated light 452$s$. Further, the light detection assembly 450 can include a third sensor zone 456 that measures a third scattered or propagated light 456$s$ within a third range of angles relative to the light beam axis 444. As shown here, the third range of angles for scattered or propagated light 456$s$ is different from both the first range of angles for scattered or propagated light 452$s$ and the second range of angles for scattered or propagated light 454$s$. The light detection assembly 450 also includes a fourth sensor zone 458 that measures axial light 458$t$ transmitted through the cells of the biological sample passing individually through the cell interrogation zone 412 or propagated from the cell interrogation zone along the axis beam. In some instances, each of the sensor zones 452, 454, 456, and 458 are disposed at a separate sensor associated with that specific sensor zone. In some instances, one or more of the sensor zones 452, 454, 456, and 458 are disposed on a common sensor of the light detection assembly 450. For example, the light detection assembly may include a first sensor 451 that includes first sensor zone 452 and second sensor zone 454. Hence, a single sensor may be used for detecting or measuring two or more types (e.g. low angle, medium angle, or high angle) of light scatter or propagation.

Figure 4A:
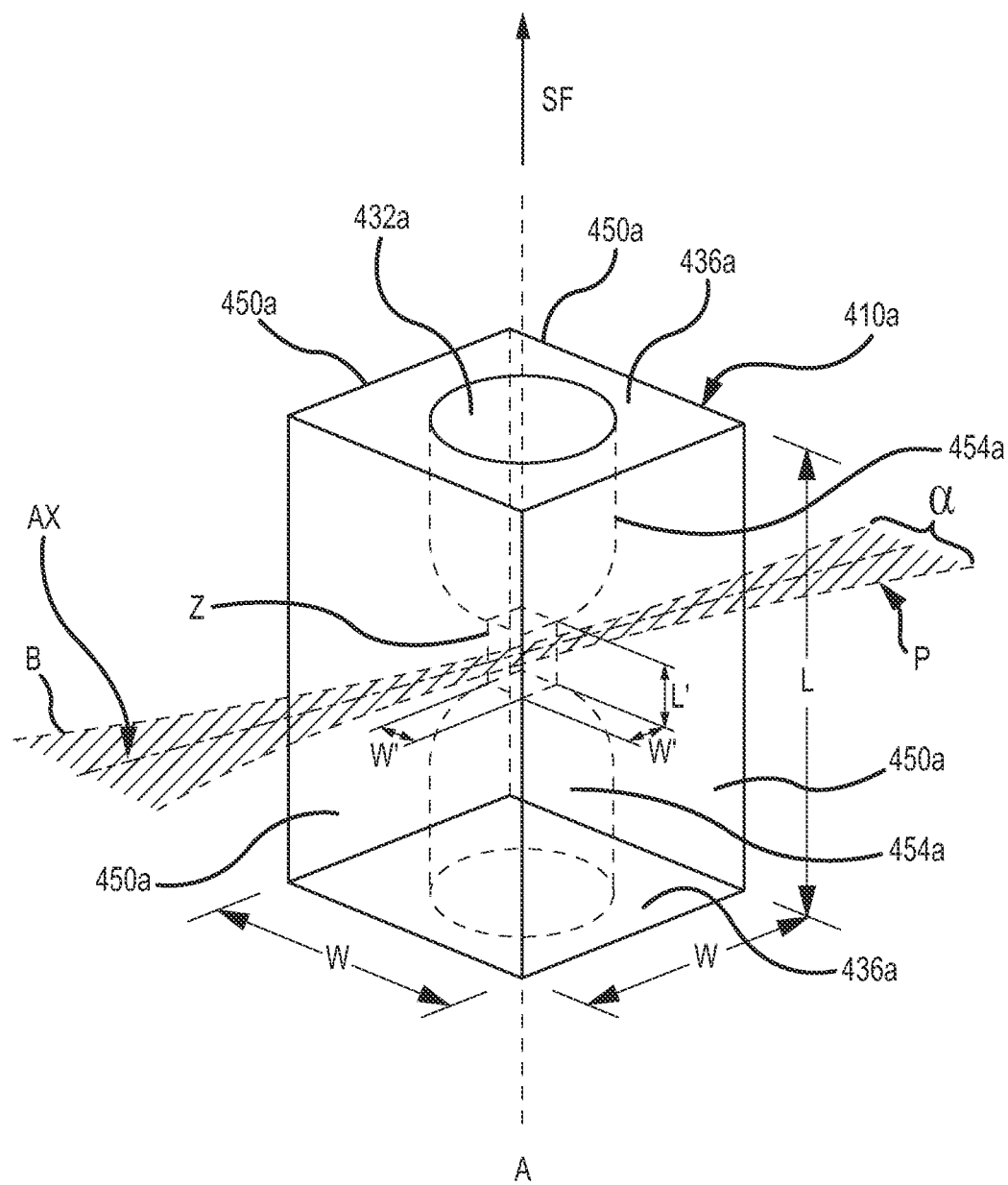
FIG. 4A shows aspects of an optical element of a cellular analysis system, according to embodiments of the present invention.

Automated cellular analysis systems may include any of a variety of optical elements or transducer features. For example, as depicted in FIG. 4A, an optical element 410$a$ of a cellular analysis system transducer may have a square prism shape, with four rectangular, optically flat sides 450$a$ and opposing end walls 436$a$. In some instances, the respective widths W of each side 450$a$ are the same, each measuring about 4.2 mm, for example. In some instances, the respective lengths L of each side 450$a$ are the same, each measuring about 6.3 mm, for example. In some instances, all or part of the optical element 410$a$ may be fabricated from fused silica, or quartz. A flow passageway 432$a$ formed through a central region of optical element 410$a$ may be concentrically configured with respect to a longitudinal axis A passing through the center of element 410$a$ and parallel to a direction of sample-flow as indicated by arrow SF. Flow passageway 432$a$ includes a cell interrogation zone Z and a pair of opposing tapered bore holes 454$a$ having openings in the vicinity of their respective bases that fluidically communicate with the cell interrogation zone. In some instances, the transverse cross-section of the cell interrogation zone Z is square in shape, the width W' of each side nominally measuring 50 microns±10 microns. In some instances, the length L' of the cell interrogation zone Z, measured along axis A, is about 1.2 to 1.4 times the width W' of the interrogation zone. For example, the length L' may be about 65 microns±10 microns. As noted elsewhere herein, DC and RF measurements can be made on cells passing through the cell interrogation zone. In some instances, the maximum diameter of the tapered bore holes 454a, measured at end walls 436a, is about 1.2 mm. An optical structure 410a of the type described can be made from a quartz square rod containing a 50×50 micron capillary opening, machined to define the communicating bore holes 454a, for example. A laser or other irradiation source can produce a beam B that is directed through or focused into the cell interrogation zone. For example, the beam may be focused into an elliptically shaped waist located within the interrogation zone Z at a location through which the cells are caused to pass. A cellular analysis system may include a light detection assembly that is configured to detect light which emanates from the optical element 410a, for example light P that is propagated from the cell interrogation zone Z which contains illuminated or irradiated cells flowing therewithin. As depicted here, light P can propagate or emanate from the cell interrogation zone Z within an angular range α, and thus can be measured or detected at selected angular positions or angular ranges relative to the beam axis AX. Relatedly, a light detection assembly can detect light scattered or axially transmitted in a forward plane within various angular ranges with respect to an axis AX of beam B. As discussed elsewhere herein, one or more light propagation measurements can be obtained for individual cells passing through the cell interrogation zone one at a time. In some cases, a cellular analysis system may include one or more features of a transducer or cell interrogation zone such as those described in U.S. Pat. Nos. 5,125,737; 6,228,652; 8,094,299; and 8,189,187, the contents of which are incorporated herein by reference.

Figure 5:
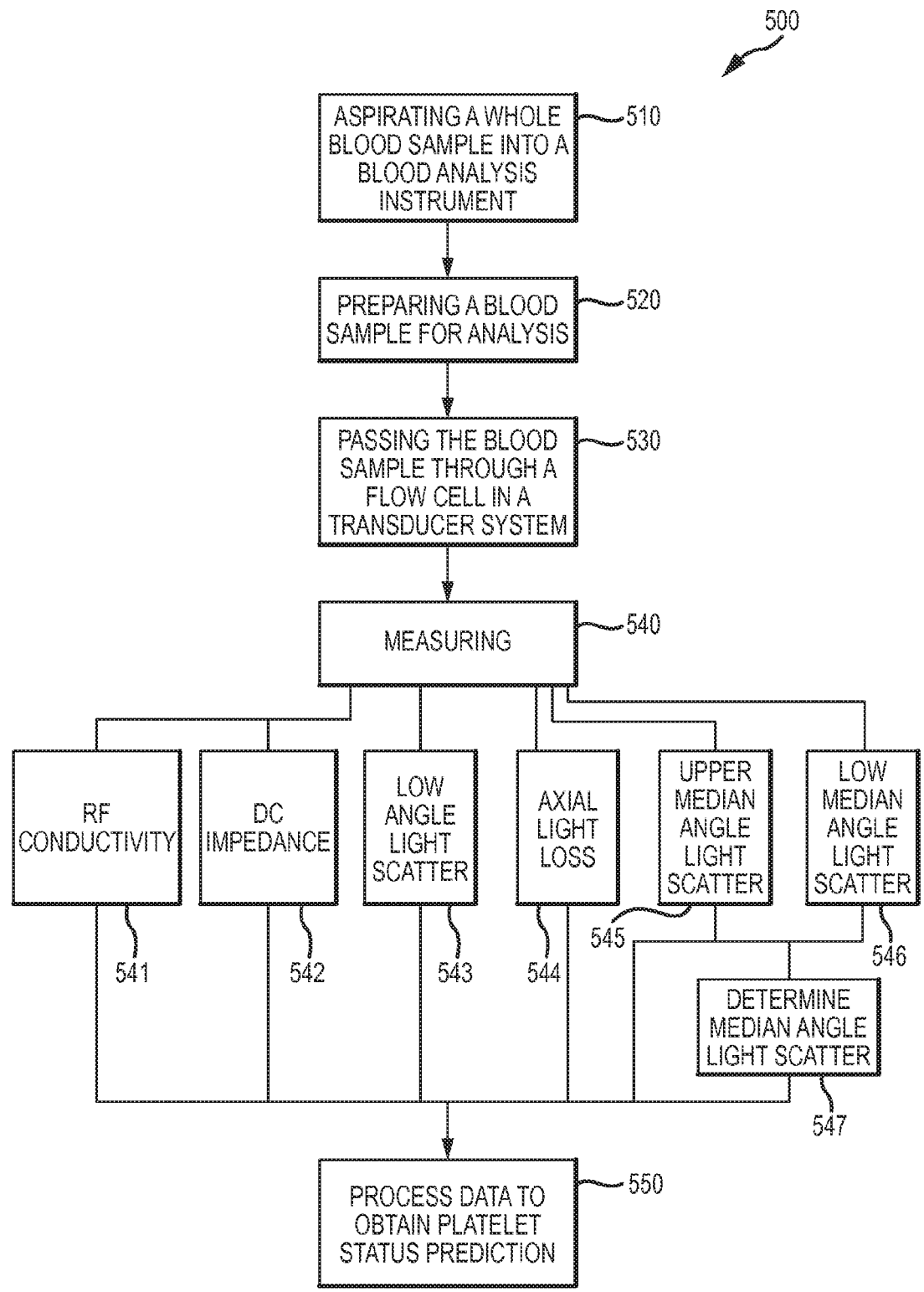
FIG. 5 depicts aspects of an exemplary method for evaluating the platelet status of an individual, according to embodiments of the present invention.

FIG. 5 depicts aspects of an exemplary method 500 for predicting or assessing a platelet status of an individual. Method 500 includes introducing a blood sample into a blood analysis system, as indicated by step 510. As shown in step 520, the method may also include preparing the blood sample by dividing the sample into aliquots and mixing the aliquot samples with appropriate reagents. In step 530, the samples can be passed through a flow cell in a transducer system such that sample constituents (e.g. blood cells) pass through a cell interrogation zone in a one by one fashion. The constituents can be irradiated by a light source, such as a laser. In step 540, any combination RF conductivity 541, DC impedance 542, first angular light propagation 543 (e.g. LALS), second angular light propagation 544 (e.g. AL2), third angular light propagation 545 (e.g. UMAL), and/or fourth angular light propagation 546 (e.g. LMALS) may be measured. As depicted by step 547, the third and fourth angular light propagation measurements can be used to determine a fifth angular light propagation measurement (e.g. MALS). Alternatively, MALS can be measured directly. As discussed elsewhere herein, certain measurements or combinations of measurements can be processed, as indicated by step 550, so as to provide a platelet status prediction. Optionally, methods may also include determining a treatment regime based on the predicted platelet status.

A cellular analysis system may be configured to correlate a subset of DC impedance, RF conductivity, angular light measurements (e.g. first scattered light, second scattered light) and the axial light measurements from the cells of the biological sample with a platelet status of an individual. As discussed elsewhere herein, in some instances at least a portion of the correlation can be performed using one or more software modules executable by one or more processors, one or more hardware modules, or any combination thereof. Processors or other computer or module systems may be configured to receive as an input values for the various measurements or parameters and automatically output the predicted platelet status of the individual. In some instances, one or more of the software modules, processors, and/or hardware modules may be included as a component of a hematology system that is equipped to obtain multiple light angle detection parameters, such as a hematology analyzer. In some instances, one or more of the software modules, processors, and/or hardware modules may be included as a component of a stand-alone computer that is in operative communication or connectivity with a hematology system that is equipped to obtain multiple light angle detection parameters, such as a hematology analyzer. In some instances, at least a portion of the correlation can be performed by one or more of the software modules, processors, and/or hardware modules that receive data from a hematology system that is equipped to obtain multiple light angle detection parameters, such as a hematology analyzer remotely via the internet or any other over wired and/or wireless communication network. Relatedly, each of the devices or modules according to embodiments of the present invention can include one or more software modules on a computer readable medium that is processed by a processor, or hardware modules, or any combination thereof.

Figure 6:
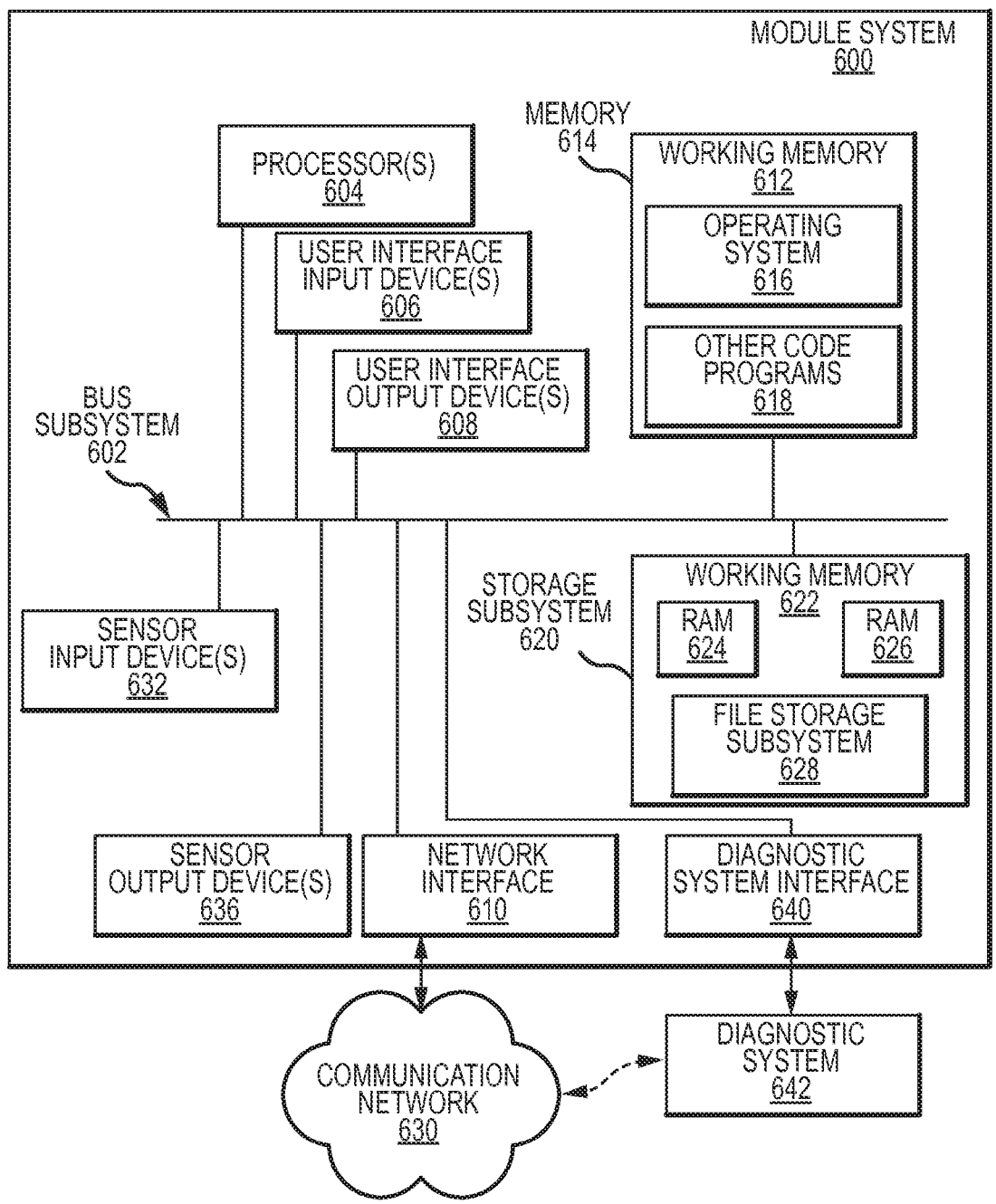
FIG. 6 provides a simplified block diagram of an exemplary module system, according to embodiments of the present invention.

FIG. 6 is a simplified block diagram of an exemplary module system that broadly illustrates how individual system elements for a module system 600 may be implemented in a separated or more integrated manner. Module system 600 may be part of or in connectivity with a cellular analysis system for predicting a platelet status of an individual according to embodiments of the present invention. Module system 600 is well suited for producing data or receiving input related to a platelet analysis. In some instances, module system 600 includes hardware elements that are electrically coupled via a bus subsystem 602, including one or more processors 604, one or more input devices 606 such as user interface input devices, and/or one or more output devices 608 such as user interface output devices. In some instances, system 600 includes a network interface 610, and/or a diagnostic system interface 640 that can receive signals from and/or transmit signals to a diagnostic system 642. In some instances, system 600 includes software elements, for example shown here as being currently located within a working memory 612 of a memory 614, an operating system 616, and/or other code 618, such as a program configured to implement one or more aspects of the techniques disclosed herein.

In some embodiments, module system 600 may include a storage subsystem 620 that can store the basic programming and data constructs that provide the functionality of the various techniques disclosed herein. For example, software modules implementing the functionality of method aspects, as described herein, may be stored in storage subsystem 620. These software modules may be executed by the one or more processors 604. In a distributed environment, the software modules may be stored on a plurality of computer systems and executed by processors of the plurality of computer systems. Storage subsystem 620 can include memory subsystem 622 and file storage subsystem 628. Memory subsystem 622 may include a number of memories including a main random access memory (RAM) 626 for storage of instructions and data during program execution and a read only memory (ROM) 624 in which fixed instructions are stored. File storage subsystem 628 can provide persistent (non-volatile) storage for program and data files, and may include tangible storage media which may optionally embody patient, treatment, assessment, or other data. File storage subsystem 628 may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 600. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 628. In some embodiments, the software or code will provide protocol to allow the module system 600 to communicate with communication network 630. Optionally, such communications may include dial-up or internet connection communications.

It is appreciated that system 600 can be configured to carry out various aspects of methods of the present invention. For example, processor component or module 604 can be a microprocessor control module configured to receive cellular parameter signals from a sensor input device or module 632, from a user interface input device or module 606, and/or from a diagnostic system 642, optionally via a diagnostic system interface 640 and/or a network interface 610 and a communication network 630. In some instances, sensor input device(s) may include or be part of a cellular analysis system that is equipped to obtain multiple light angle detection parameters, such as a hematology analyzer. In some instances, user interface input device(s) 606 and/or network interface 610 may be configured to receive cellular parameter signals generated by a cellular analysis system that is equipped to obtain multiple light angle detection parameters, such as a hematology analyzer. In some instances, diagnostic system 642 may include or be part of a cellular analysis system that is equipped to obtain multiple light angle detection parameters, such as a hematology analyzer.

Processor component or module 604 can also be configured to transmit cellular parameter signals, optionally processed according to any of the techniques disclosed herein, to sensor output device or module 636, to user interface output device or module 608, to network interface device or module 610, to diagnostic system interface 640, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, MacIntosh, and Unix, along with any of a variety of commonly used programming languages, may be used to implement embodiments of the present invention.

User interface input devices 606 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 606 may also download a computer executable code from a tangible storage media or from communication network 630, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 600.

User interface output devices 606 may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 600 to a user.

Bus subsystem 602 provides a mechanism for letting the various components and subsystems of module system 600 communicate with each other as intended or desired. The various subsystems and components of module system 600 need not be at the same physical location but may be distributed at various locations within a distributed network. Although bus subsystem 602 is shown schematically as a single bus, alternate embodiments of the bus subsystem may utilize multiple busses.

Network interface 610 can provide an interface to an outside network 630 or other devices. Outside communication network 630 can be configured to effect communications as needed or desired with other parties. It can thus receive an electronic packet from module system 600 and transmit any information as needed or desired back to module system 600. As depicted here, communication network 630 and/or diagnostic system interface 642 may transmit information to or receive information from a diagnostic system 642 that is equipped to obtain multiple light angle detection parameters, such as such as a hematology analyzer.

In addition to providing such infrastructure communications links internal to the system, the communications network system 630 may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 600 itself can be of varying types including a computer terminal, a personal computer, a portable computer, a workstation, a network computer, or any other data processing system. Due to the ever-changing nature of computers and networks, the description of module system 600 depicted in FIG. 6 is intended only as a specific example for purposes of illustrating one or more embodiments of the present invention. Many other configurations of module system 600 are possible having more or less components than the module system depicted in FIG. 6. Any of the modules or components of module system 600, or any combinations of such modules or components, can be coupled with, or integrated into, or otherwise configured to be in connectivity with, any of the cellular analysis system embodiments disclosed herein. Relatedly, any of the hardware and software components discussed above can be integrated with or configured to interface with other medical assessment or treatment systems used at other locations.

In some embodiments, the module system 600 can be configured to receive one or more cellular analysis parameters of a patient at an input module. Cellular analysis parameter data can be transmitted to an assessment module where a platelet status is predicted or determined. The predicted platelet status can be output to a system user via an output module. In some cases, the module system 600 can determine an initial treatment or induction protocol for the patient, or an adjusted treatment protocol, based on one or more cellular analysis parameters and/or the predicted platelet status, for example by using a treatment module. The treatment can be output to a system user via an output module. Optionally, certain aspects of the treatment can be determined by an output device, and transmitted to a treatment system or a sub-device of a treatment system. Any of a variety of data related to the patient can be input into the module system, including age, weight, sex, treatment history, medical history, and the like. Parameters of treatment regimens or diagnostic evaluations can be determined based on such data.

Relatedly, in some instances a system includes a processor configured to receive VCS data as input. A processor may also be configured to receive CBC data as input. Optionally, a processor, storage medium, or both, may be incorporated within a hematology or cellular analysis machine. In some instances, the hematology machine may generate VCS data, CBC data, or other information for input into the processor. In some instances, a processor, a storage medium, or both, can be incorporated within a computer, and the computer can be in communication with a hematology machine. In some instances, a processor, a storage medium, or both, can be incorporated within a computer, and the computer can be in remote communication with a hematology machine via a network.

Volume Conductivity Scatter (VCS) Data

In addition to CBC data, which may be obtained from a CBC module, VCS data may be obtained from a VCS module. Exemplary VCS parameters include the following:
1. Cell Conductivity (C) [high frequency current]
2. Cell Volume (V) [low frequency current]
3. Axial light loss or absorbed light (AL2 or ALL)
4. Low-angle light scatter (LALS)
5. Upper median-angle light scatter (UMALS)
6. Lower median-angle light scatter (LMALS)
7. Median-angle light scatter (MALS) [UMALS+LMALS]

In this way, various parameters (e.g. volume, conductivity, and angles of light scatter or propagation) can be calculated separately for blood cells such as white blood cells, red blood cells, and platelets. This data can be obtained based on a biological sample of an individual. What is more, CBC and VCS data can be viewed on the screen of an instrument, such as that depicted in FIG. 7, as well as automatically exported as an Excel file. Hence, blood cells (e.g. RBC's, platelets, and WBC's) can be analyzed and individually plotted in tri-dimensional histograms, with the position of each cell on the histogram being defined by certain parameters as described herein.

Figure 7:
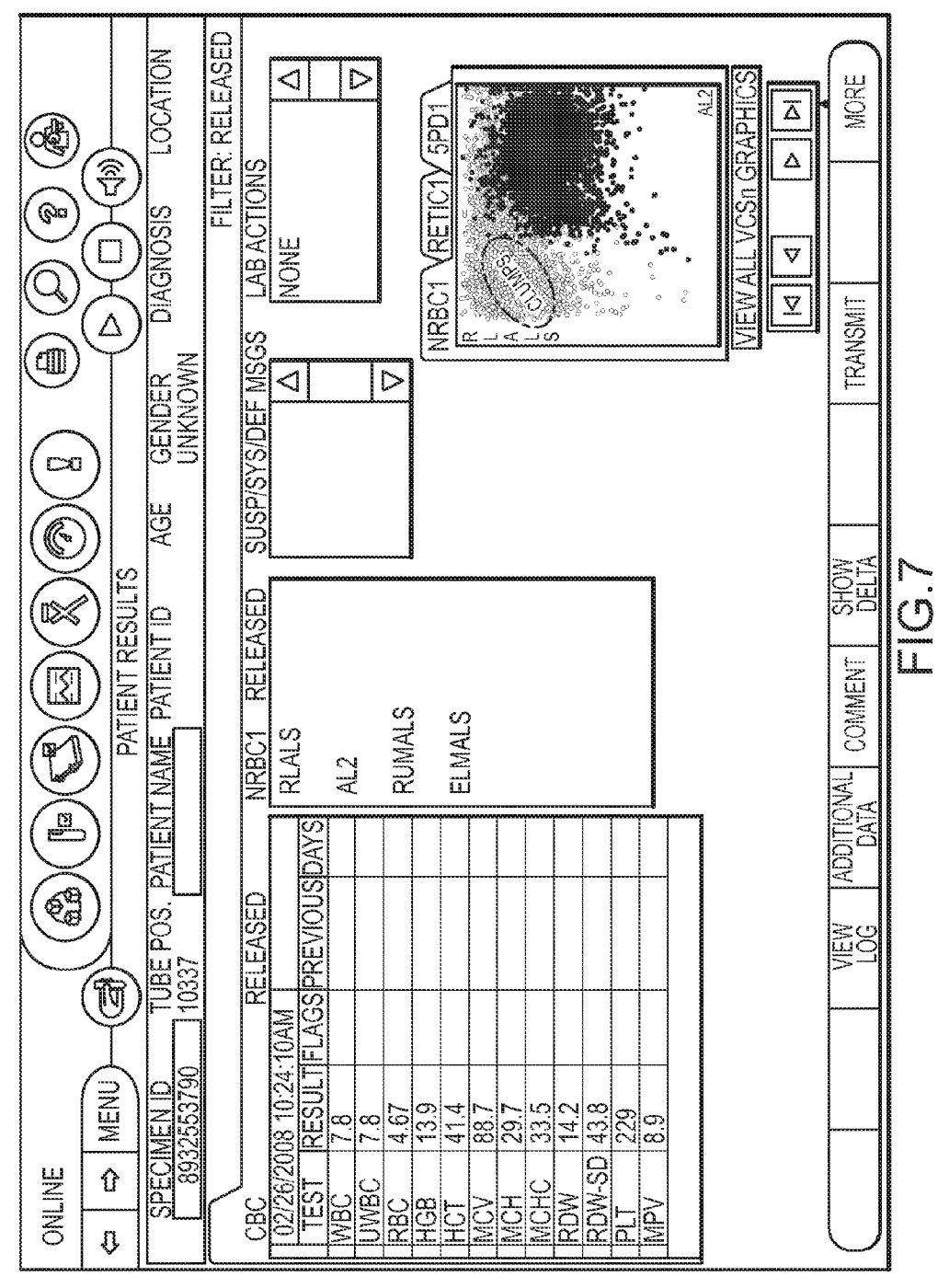

Subpopulations of cells or particles can be separated into different groups at different locations on the histograms. For example, platelet clumps and white blood cells can be clustered in different regions of a histogram, thus forming cell populations. FIG. 7 depicts an exemplary screen shot of aspects of a count analysis. As illustrated here, platelet clump events are encircled on the histogram. Generally, such histograms can be obtained from a nucleated red blood cell (NRBC) channel (or a WBC differential channel or a reticulocyte channel) as discussed elsewhere herein.

Such VCS values can correspond to the position of the population in the histogram, and to the morphology of the blood cells under the microscope. As depicted in FIGS. 7D to 7F, certain channel modules can provide measurements for various particles or blood components, such as platelet clumps, blood cells, or cellular debris which may be present.

VCS parameters can be used to analyze cellular events in a quantitative, objective, and automated manner, free from the subjectivity of human interpretation, which is also very time consuming, expensive, and has limited reproducibility. In certain embodiments, VCS parameters can be used in estimating a platelet count in an individual based on a biological sample obtained from the individual, and in the diagnosis of various medical conditions that alter the platelet counts. It is understood that when referring to VCS parameters or volume conductivity scatter data profiles, such characterizations may include a subset of the individual VCS data features. For example, VCS parameter data may include a combination of volume and conductivity measures, a combination of volume and scatter measures, or a combination of conductivity and scatter measures. Similarly, VCS parameter data may include a volume measure only, a conductivity measure only, or a scatter measure only. In some instances, VCS parameter data may be considered to include a set or subset of light propagation and current data. For example, the light propagation measures may include a first propagated light at a first angle, a second propagated light at a second angle different from the first angle, an axial propagated light, or any combination thereof. Relatedly, the current measures may include a low frequency current (e.g DC impedance corresponding to volume), a high frequency current (e.g. RF conductivity corresponding to internal cellular density), or a combination thereof. In this sense, VCS parameter data or volume conductivity scatter data profiles may be referred to as current light propagation parameters or data profiles.

As further discussed herein, it has been discovered that certain VCS parameter values are highly useful for assessing a platelet status in an individual. Accordingly, these parameters can be implemented in systems and methods for the estimation of platelet count in an individual, and for the diagnosis of platelet-related conditions.

Corrected Platelet Count (Method I)

Figure 7A:
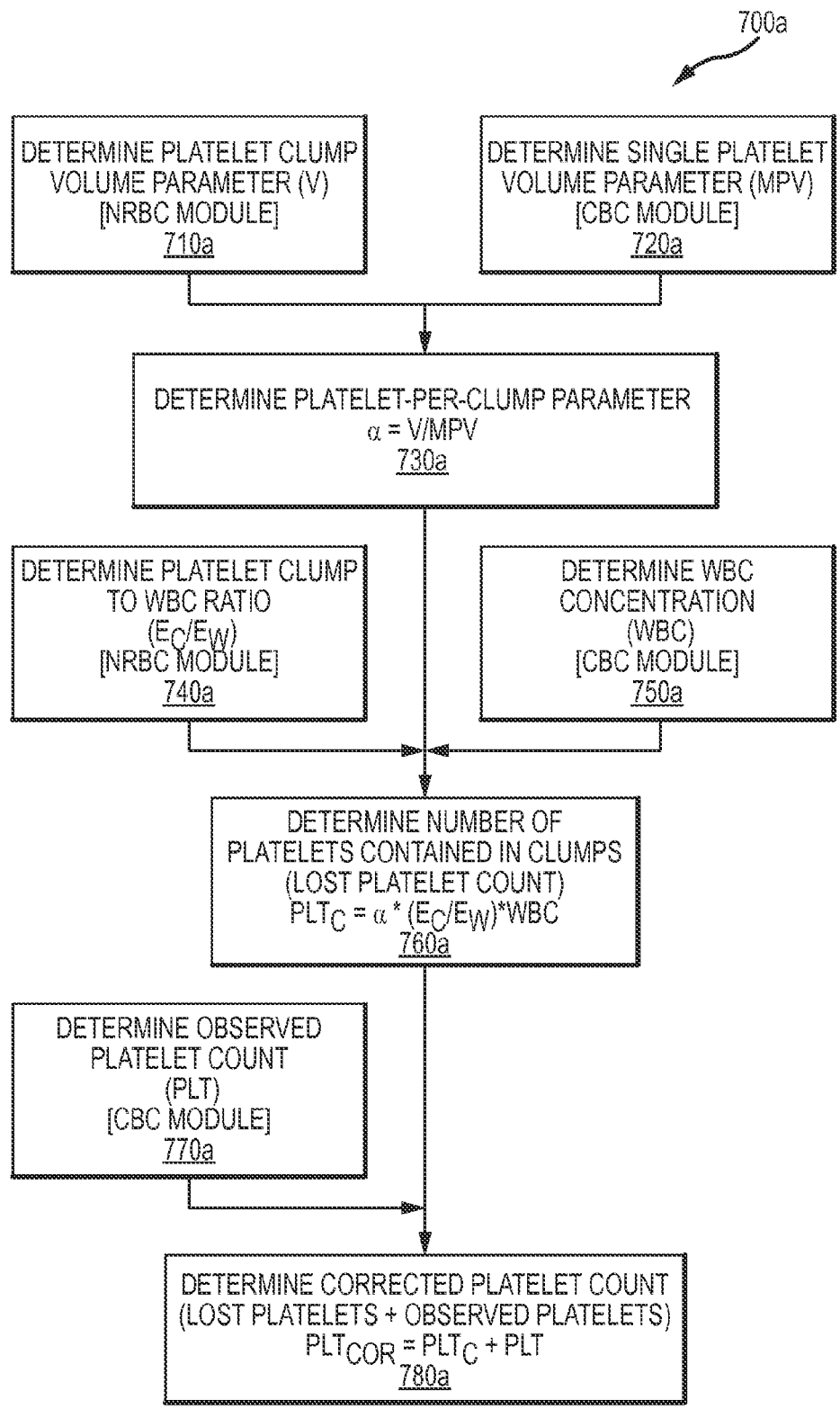
FIGS. 7A to 7J schematically shows aspects of techniques for obtaining blood cell parameters, according to embodiments of the present invention.

FIG. 7A illustrates aspects of an exemplary method 700a for determining a corrected platelet count, according to embodiments of the present invention. As shown here, the method may include determining or obtaining a platelet clump volume parameter, as depicted in step 710a, determining or obtaining a single platelet volume parameter, as depicted in step 720a, and determining or obtaining a platelet per clump parameter, as depicted in step 730a. The platelet per clump parameter can be based on the platelet clump volume parameter and the single platelet volume parameter.

Further, the method may include determining or obtaining a platelet clump to WBC ratio parameter, as depicted in step 740a, determining or obtaining a WBC concentration parameter, as depicted in step 750a, and determining or obtaining the number of platelets contained in clumps (e.g. the lost platelet count), as depicted in step 760a. The estimation of the number of platelets contained in clumps can be based on the platelet clump to WBC parameter, the platelet per clump parameter, and the WBC concentration parameter.

What is more, the method may include determining or obtaining the observed platelet count, as depicted in step 770a, and determining or estimating the corrected platelet count, as depicted in step 780a. The calculation of the corrected platelet count can be based on the observed platelet count and the lost platelet count. For example, the estimated corrected platelet count can be based on the sum of the observed platelet events and the estimated number of platelets contained in clumps.

Determining Platelet Clump Volume Parameter

Figure 7B:
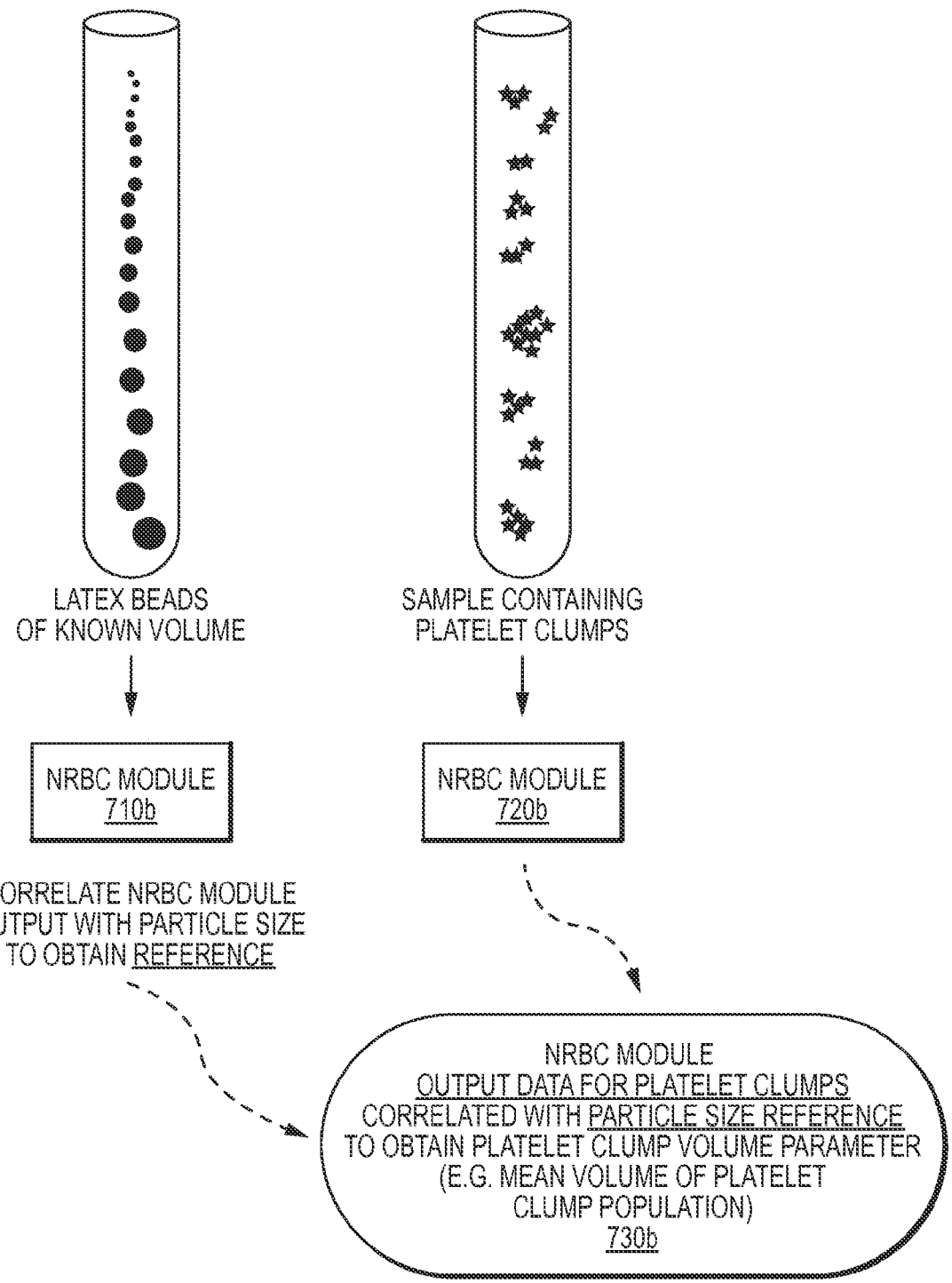

FIG. 7B depicts aspects of a technique for determining a platelet clump volume parameter, according to embodiments of the present invention. As shown here, the method includes determining a channel-volume relationship by analyzing latex beads of known volume using an NRBC module, as depicted step 710b. Typically, in an NRBC module, the direct current (DC) is directly proportional to the particle size. Hence, larger DC pulses correspond to larger particle sizes. In this way, it is possible to obtain a reference or standard that correlates NRBC channel values with particle volume values.

Further, the method includes processing a sample containing platelet clumps using an NRBC module, as depicted in step 720b. For example, the mean channel from a 1-D histogram of the platelet clump population can be calculated.

The NRBC module output data for the platelet clumps can be correlated with the particle size reference to obtain a platelet clump volume parameter, such as a mean volume of the platelet clump population. For example, a channel-volume relationship (e.g from step 710b) and a mean channel (e.g. from step 720b) can be used to determine a mean volume (e.g. in femtoliters) of the platelet clump population, V (e.g. step 730b). In some instances, the platelet clumps present in the sample present a population distribution, such that different clumps include different numbers of platelets. For example, some clumps of the population may include 5 platelets, some clumps may include 10 platelets, some clumps may include 20 platelets, and so on.

An exemplary approach for determining a platelet clump volume parameter is depicted as step 710a of FIG. 7A.

Determining Single Platelet Volume Parameter

Figure 7C:
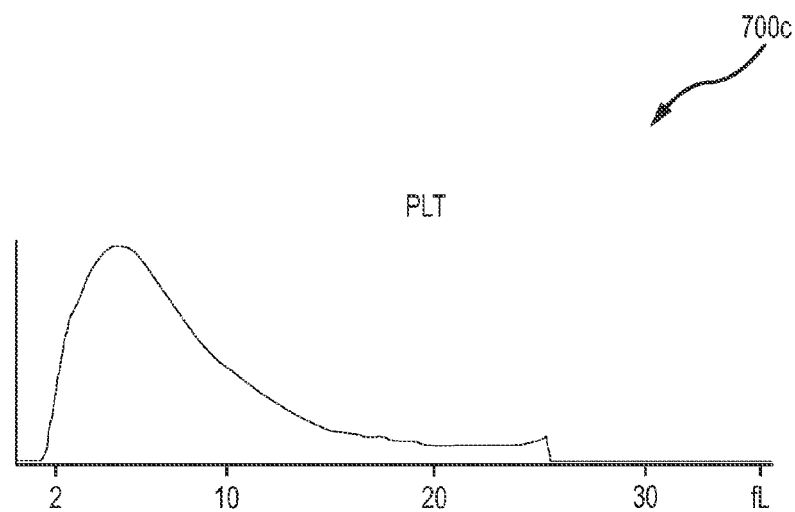
Figure 7D:
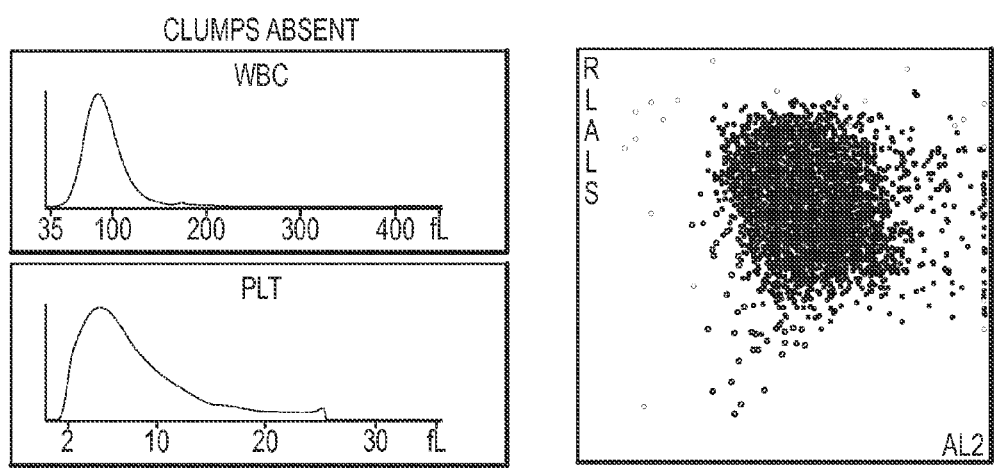
Figure 7E:
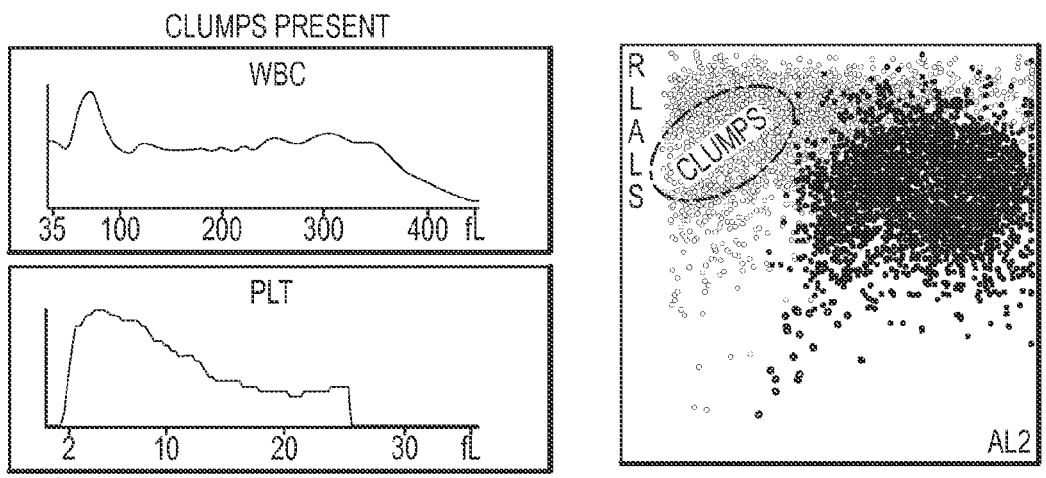
Figure 7F:
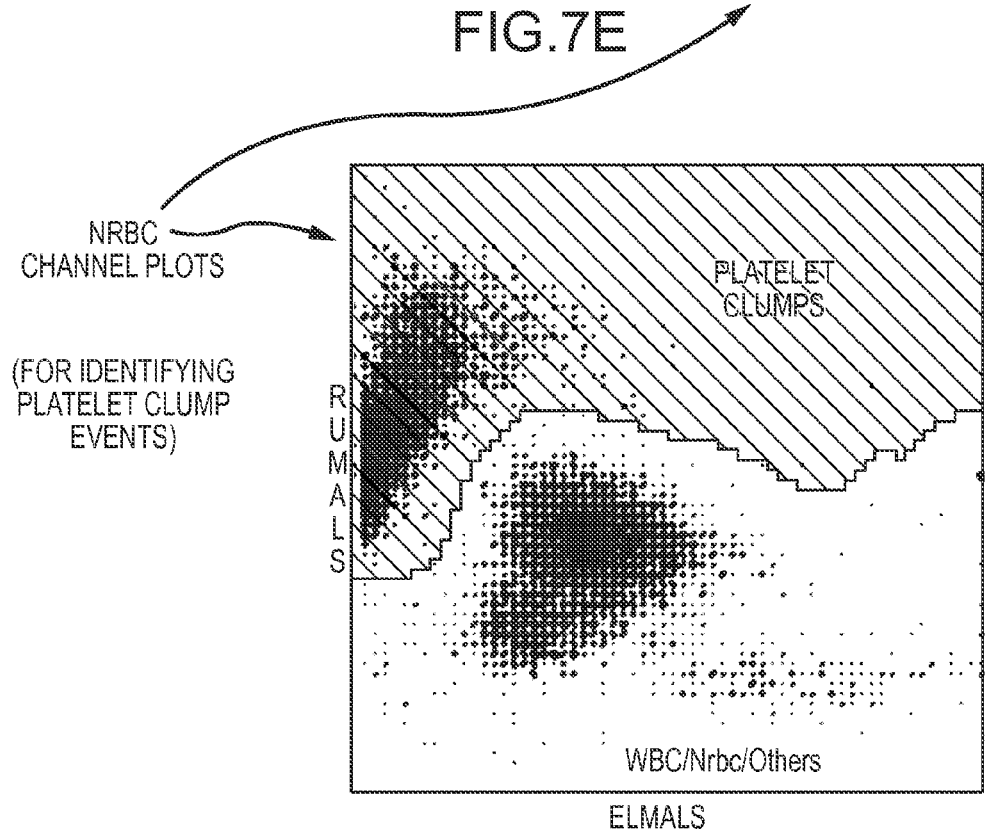

FIG. 7C depicts aspects of a technique for determining a single platelet volume parameter, according to embodiments of the present invention. As shown here, a platelet population histogram 700c can be obtained from a CBC module. The curve illustrates a single platelet volume distribution, in femtoliters. The average or mean platelet volume for this distribution can be referred to as MPV. Calculation of the mean may involve, for each channel, multiplying the number of events in the channel by the volume which corresponds to the channel. The results can be summed across all channels, and then divided by the total number of events observed to obtain the average volume (MPV) for each event.

An exemplary approach for determining a single platelet volume parameter is depicted as step 720a of FIG. 7A.

Determining Platelet Per Clump Parameter

It is possible to obtain the average number of platelets contained in each platelet clump of a sample, by dividing a platelet clump volume parameter (e.g. V) by a single platelet volume parameter (e.g. MPV). Such a measure can indicate the number of platelets contained in one platelet clump, on average. An exemplary method for estimating a platelet per clump parameter can be based on the following equation: $\alpha = V/MPV$.

Hence, a platelet clump volume parameter and a single platelet volume parameter can be used to obtain the average number of platelets contained in each platelet clump. Relatedly, the average number of platelets contained in each platelet clump can be calculated by dividing the mean volume of platelet clump population (V) by a mean platelet volume (MPV). In this way, embodiments of the present invention encompass techniques for using information from NRBC and CBC modules to estimate the number of platelets in a single clump, for example by calculating on average the number of platelets per clump.

An exemplary approach for determining a platelet per clump parameter is depicted as step 730a of FIG. 7A.

Determining Platelet Clump to White Blood Cell Ratio Parameter

Platelet clump events can be delineated or segmented from other events (e.g. NRBC, WBC, platelets, and various forms of debris) by implementing certain analysis techniques in an NRBC module, such as the NRBC module of a hematology analyzer. For example, the absence or presence of platelet clumps can be seen in an RLALS-vs-AL2 plot view from an NRBC module as depicted by FIG. 7D (right panel, little or no platelet clumping) and FIG. 7E (right panel, significant platelet clumping). The left panels of FIGS. 7D and 7E provide CBC module volume distribution histograms for White Blood Cell (WBC) and Platelet (PLT) events, corresponding to those shown in the right panels. As depicted in FIG. 7E, the CBC module histograms, for both WBC and PLT parameters, include platelet clump events. For example, the WBC histogram includes a combination of the platelet clumps and the WBC population, and the PLT histogram includes a combination of the platelet clumps and a single platelet population.

It can be seen that modules of a cellular analysis system such as a hematology analyzer can be used to evaluate any of a variety of particles in a biological sample obtained from an individual, including cells, clumps of cells, portions of cells, and other particles contained in the sample. Although the instant disclosure sometimes refers to the use of a cellular analysis system (and modules thereof) such as a hematology analyzer for analyzing events corresponding to a single cell, it is understood that the instant disclosure also encompasses the use of a cellular analysis system (and modules thereof) such as a hematology analyzer for analyzing events corresponding to any types of particles, or clumps of particles (e.g. platelet clumps) that may be contained in a biological sample obtained from an individual.

As illustrated in FIGS. 7D and 7E, a low angle light scatter (LALS) measurement can be transformed using an ARCTAN function, and represented as a Rotated LALS (RLALS) parameter. RLALS can be provided by a function of f(DC, LALS). In one embodiment, an RLALS parameter is provided by the equation: RLALS=(C) ARCTAN (DC/LALS) where (C) is a proportionality constant and (DC) is a DC current value.

In addition to the RLALS-vs-AL2 view of FIGS. 7D and 7E, it has been discovered that a RUMALS-vs-ELMALS plot presented by an NRBC channel such as that depicted in FIG. 7F provides a reliable segmentation of the platelet clumps events from other types of events.

As illustrated in FIG. 7F, an upper median-angle light scatter (UMALS) measurement can be transformed using an ARCTAN function, and represented as a Rotated UMALS (RUMALS) parameter. RUMALS can be provided by a function of f(DC, UMALS). In one embodiment, a RUMALS parameter is provided by the equation: RUMALS=(C) ARCTAN (DC/UMALS) where (C) is a scaling factor and (DC) is a DC current value.

Hence, using NRBC plot views such as those shown in FIGS. 7E and 7F, it is possible to conveniently view various particle populations and identify and segment platelet clump events relative to white blood cell events.

The ELMALS parameter may also be referred to as an extended lower median angle light scatter parameter, and can be calculated as LMALS/2.

Using 2-dimensional parameter combinations as shown in FIGS. 7E and 7F, a segmentation can be made using a non-linear boundary to separate and identify the platelet clumps from other types of events in the NRBC module. Watershed image processing technology can be applied to draw the boundary on the 2-dimensional space. Such imaging processing techniques involve implementing certain cell population searching protocols. For example, the technique may include digitally flooding the dataplot, accenting certain populations and exposing populations which may otherwise be unrecognized. By exposing smaller subpopulations, this approach can determine where the subpopulation belongs and how to apply appropriate gating techniques. In this way, it is possible to identify platelet clump events in a segmentation process.

Hematology evaluations may involve simultaneous multiparametric analysis of thousands of particles per second by suspending cells in a stream of fluid and passing them by an electronic detection apparatus. The data generated can be plotted into histograms and divided into regions. Regions are shapes that are drawn or positioned around a population of interest on a one or two parameter histogram. Exemplary region shapes include two dimensional polygons, circles, ellipses, irregular shapes, or the like. Individual events exemplified in the data correspond to unique combinations of parameters, and are accumulated in cases where multiple instances of such combinations are present. According to some embodiments, the data accumulated into histograms can be separated or clustered based on VCS parameters, in steps known as "gating" involving one or more regions. Various manual, automated, and other gating, boundary decision, region placement, or histogram segmentation techniques can also be used to identify and/or segment platelet clump data such as that shown in FIGS. 7E and 7F, and exemplary techniques are discussed in US Patent Publication No. 2010/0111400 ("Non-Linear Histogram Segmentation for Particle Analysis"), the content of which is incorporated herein by reference. According to some embodiments, various histogram analysis steps can be performed based on NRBC module and channel processing techniques using a system such as a hematology analyzer.

Hence, as shown in FIGS. 7D to 7F, the embodiments of the instant invention encompass various techniques for correlating NRBC module channel output data to the identification of platelet clump events in a biological sample. In this way, it is possible to obtain a platelet clump to WBC ratio, or to otherwise separate out the platelet clump population from other events (e.g. WBC). For example, this technique can provide a measure of the number of platelet clump events per 100 white blood cell events.

An exemplary approach for determining a platelet clump to WBC parameter is depicted as step 740a of FIG. 7A.

Determining White Blood Cell Parameter

According to some embodiments, a white blood cell concentration parameter can be obtained via a CBC module. In this way, it is possible to evaluate the number of white blood cell events corresponding to a unit volume of sample.

An exemplary approach for determining a WBC concentration parameter is depicted as step 750a of FIG. 7A.

Determining Number of Platelets Lost Due to Clumping

Once a platelet clump to WBC ratio parameter, a platelet clump parameter, and a WBC concentration parameter (e.g. steps 740a, 730a, and 750a, respectively, of FIG. 7A) are obtained, it is possible to determine or estimate the number of platelets contained in clumps, which are lost during platelet counting.

According to some embodiments, the platelet count lost to clumps, or $PLT_C$, can be calculated with the following equation: $PLT_C = \alpha*(E_C/E_W)*WBC$, where $E_C$ and $E_W$ are the number of events of platelet clump and white blood cells, respectively, in the NRBC module. Here, WBC is the white blood cell concentration from the CBC module.

An exemplary approach for determining the number of platelets contained in clumps is depicted at step 760a of FIG. 7A.

Determining Observed Platelet Count

According to some embodiments, an observed platelet count can be obtained via a CBC module. Such CBC platelet counts, however, may not include a count of platelets occurring in clumps, thus producing an artificially low platelet count. Put differently, the observed platelet count may refer to the number of unclumped platelets in a sample.

An exemplary approach for determining an observed platelet count parameter is depicted as step 770a of FIG. 7A.

Determining Corrected Platelet Count

According to some embodiments, a corrected platelet count can be determined by combining an observed platelet count parameter with a lost platelet count parameter. For example, the corrected platelet count can be calculated with the following equation: $PLT_{COR}=PLT_C+PLT$, where PLT is the observed platelet count from a CBC module.

An exemplary approach for determining a corrected platelet count parameter is depicted as step 780a of FIG. 7A.

Figure 7G:
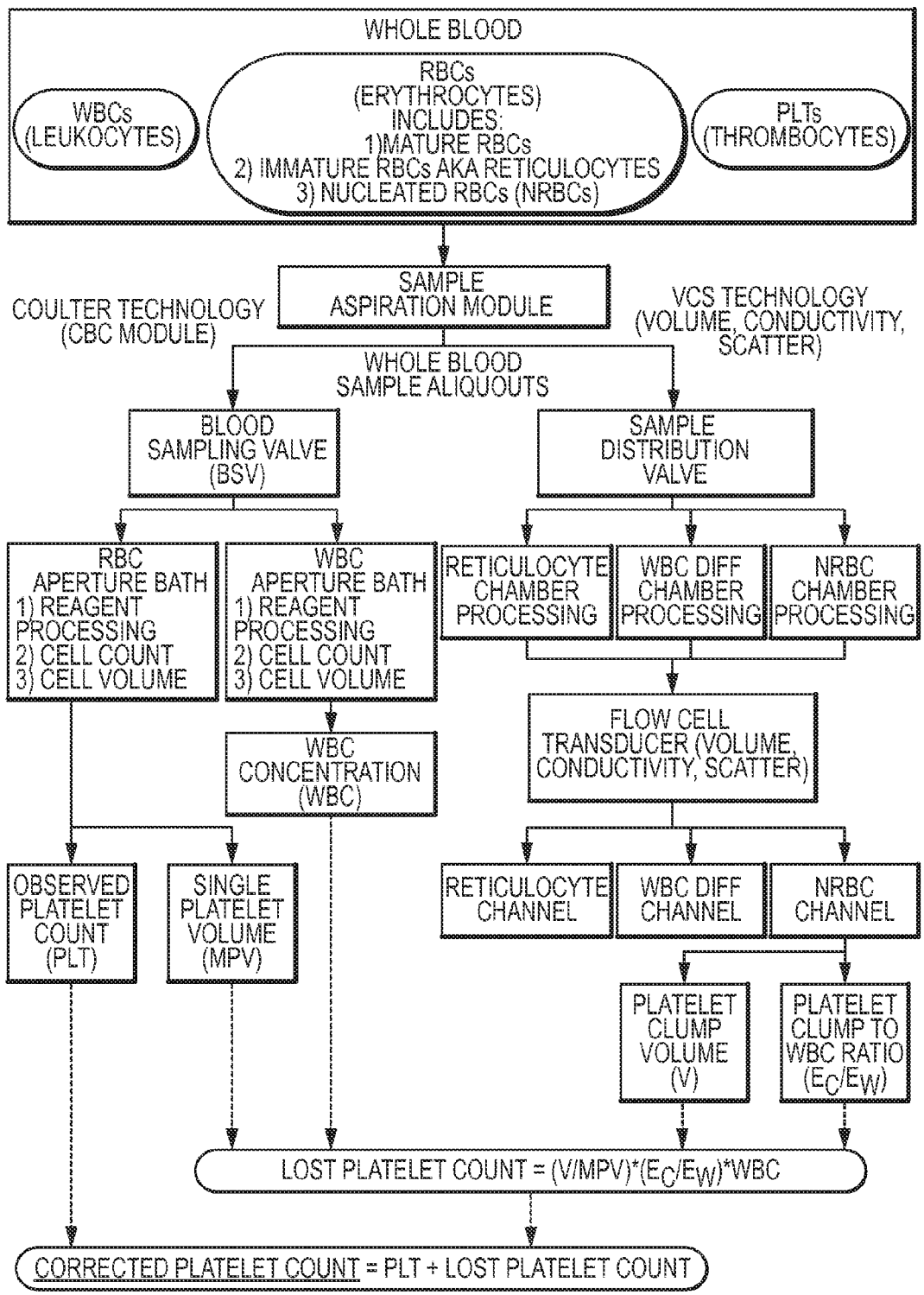

FIG. 7G illustrates aspects of a biological sample analysis system, according to embodiments of the present invention. As depicted here, platelet analysis techniques may include determining platelet clump volume and platelet clump to WBC ratio parameters using NRBC channel output from a VCS module. Further, techniques may include determining observed platelet count, single platelet volume, and WBC concentration parameters using a CBC module. What is more, techniques may include determining lost platelet count and corrected platelet count parameters using various combinations of parameters from NRBC and CBC modules.

Based on the platelet count correction techniques discussed above with regard to FIGS. 7A to 7G, it can be seen that embodiments of the present invention encompass effective systems and methods for enumerating and differentiating platelets in a blood sample using a particle analyzer. Exemplary techniques involve estimating a corrected platelet count by estimating platelet numbers contained in platelet clumps, and then adding this estimated value to the actual number of platelets counted in order to arrive at a total platelet count (corrected). In this way, clump artifacts in platelet measurements which may otherwise be lost in automated systems (thereby providing an inaccurate count, or requiring time consuming manual measurements) can be accounted for, and the platelet count adjusted appropriately. For example, platelet and platelet clumps can be detected by plotting rotated low angle light scatter versus forward excitation (e.g. FIG. 7E), or by plotting rotated upper medium angle light scattering versus low medium angle light scatter (e.g. FIG. 7F). The technique for approximating total platelet numbers as describe above involves determining the mean volume of platelet clumps (e.g. overall mean volume of the platelet clump population), deriving an estimated platelet number by dividing the clump volume value by the mean volume of a platelet, and multiplying this number by the estimated number of clumps that takes into account the white blood cell number. This estimated number can then be added to the actual number of platelets detected to arrive at a corrected platelet count.

In addition to the corrected platelet count technique discussed above, embodiments of the present invention encompass other the use of other techniques which also involve estimating a corrected platelet count by estimating platelet numbers contained in platelet clumps, and then adding this estimated value to the actual number of platelets counted in order to arrive at a total platelet count (corrected). For example, the platelet count corrected technique discussed below involves using a platelet clump calculation as described above, in addition to parameters from a nucleated red blood cell module, and probability distribution functions. Accordingly, embodiments of the present invention provide approaches for achieving corrected platelet counts which involve unique techniques for quantifying platelets within the clumps and means for providing a corrected platelet count. Similarly, embodiments of the present invention encompass the use of a cellular analysis system, such as a hematology analyzer, to identify platelet clumps from an NRBC module, calculate a platelet count lost to clumps, and add this lost count number to a reported or observed platelet count, so as to obtain a corrected platelet count.

Corrected Platelet Count (Method II)

Figure 7H:
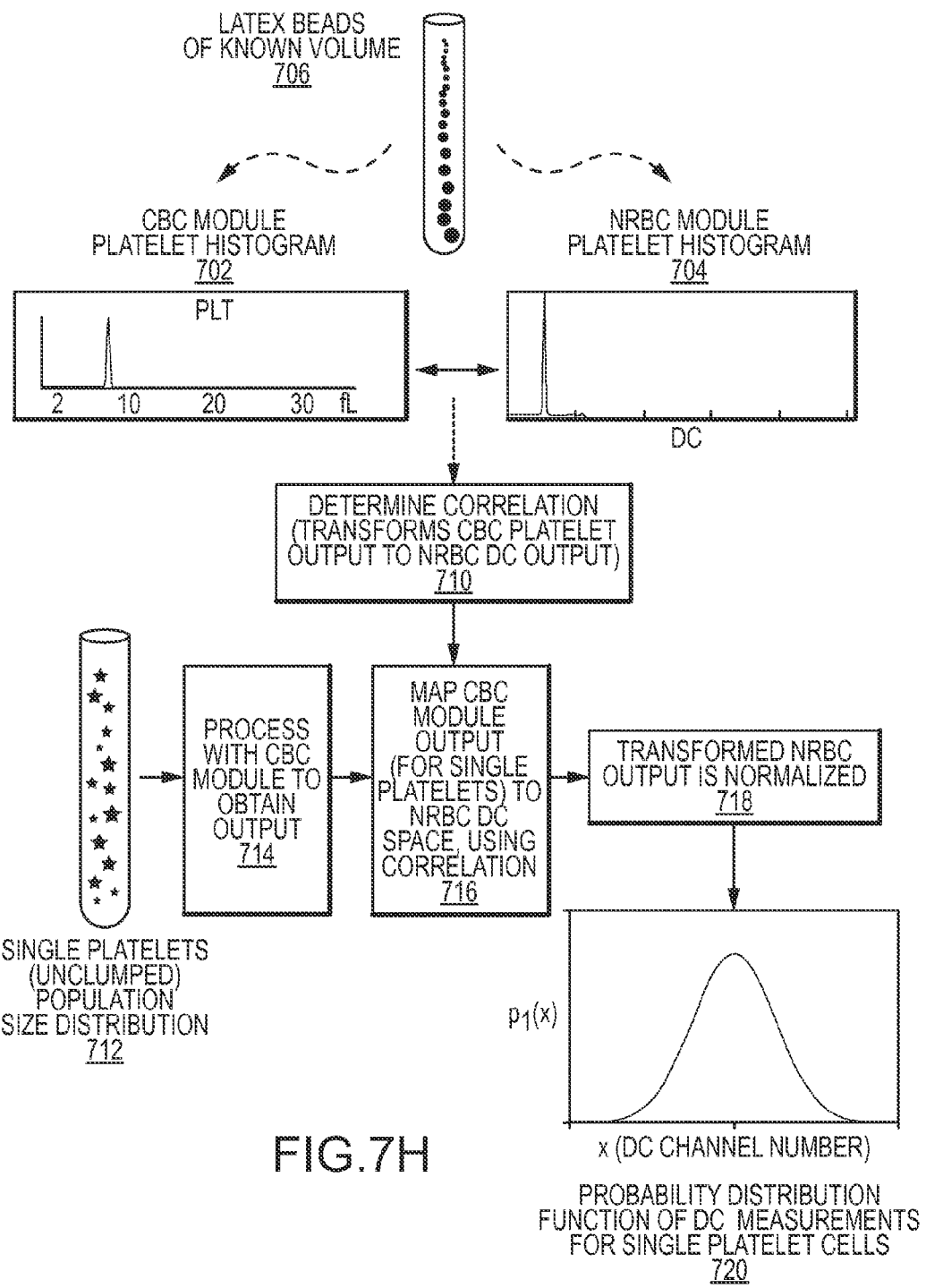
Figure 7I:
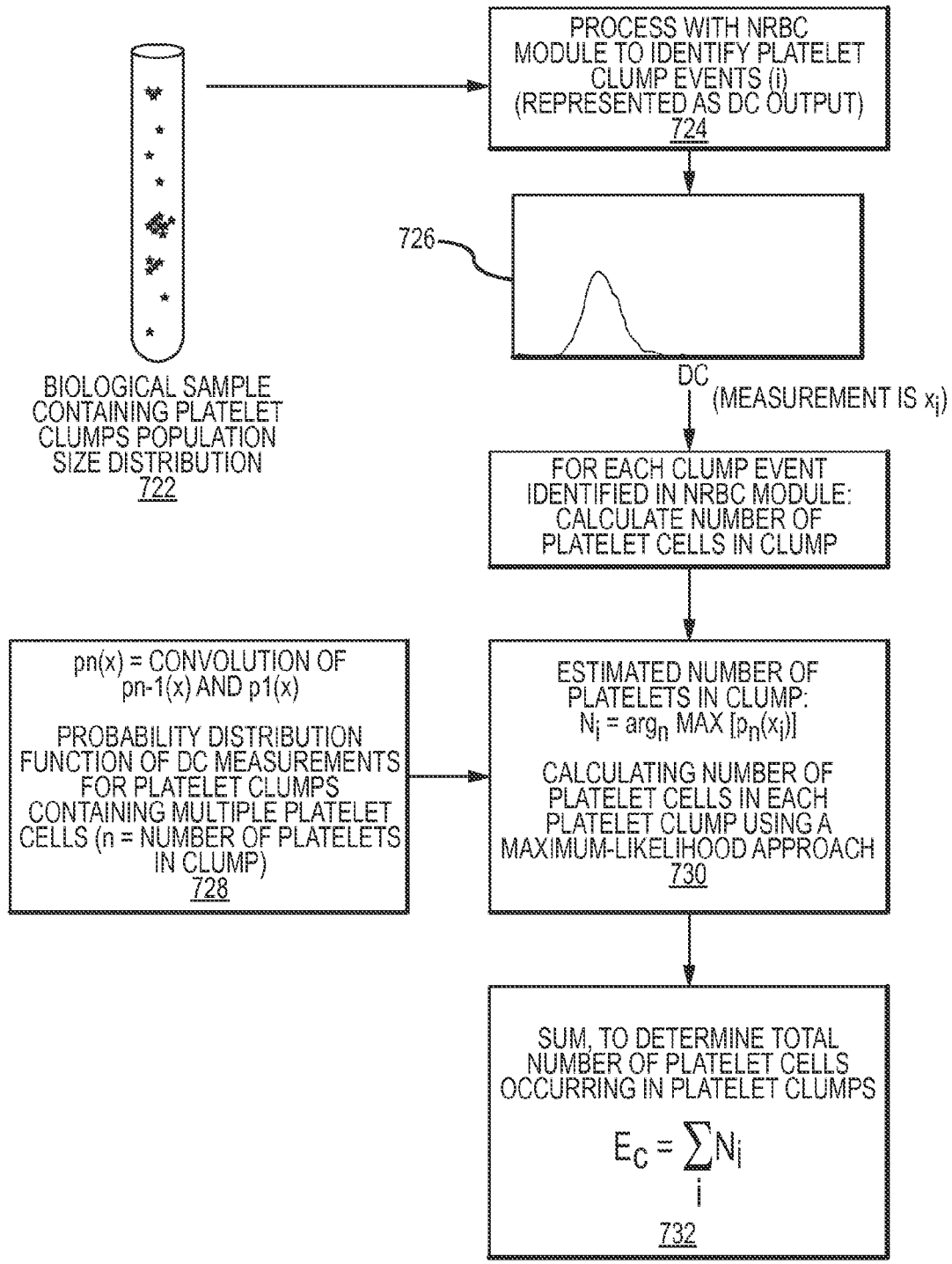
Figure 7J:
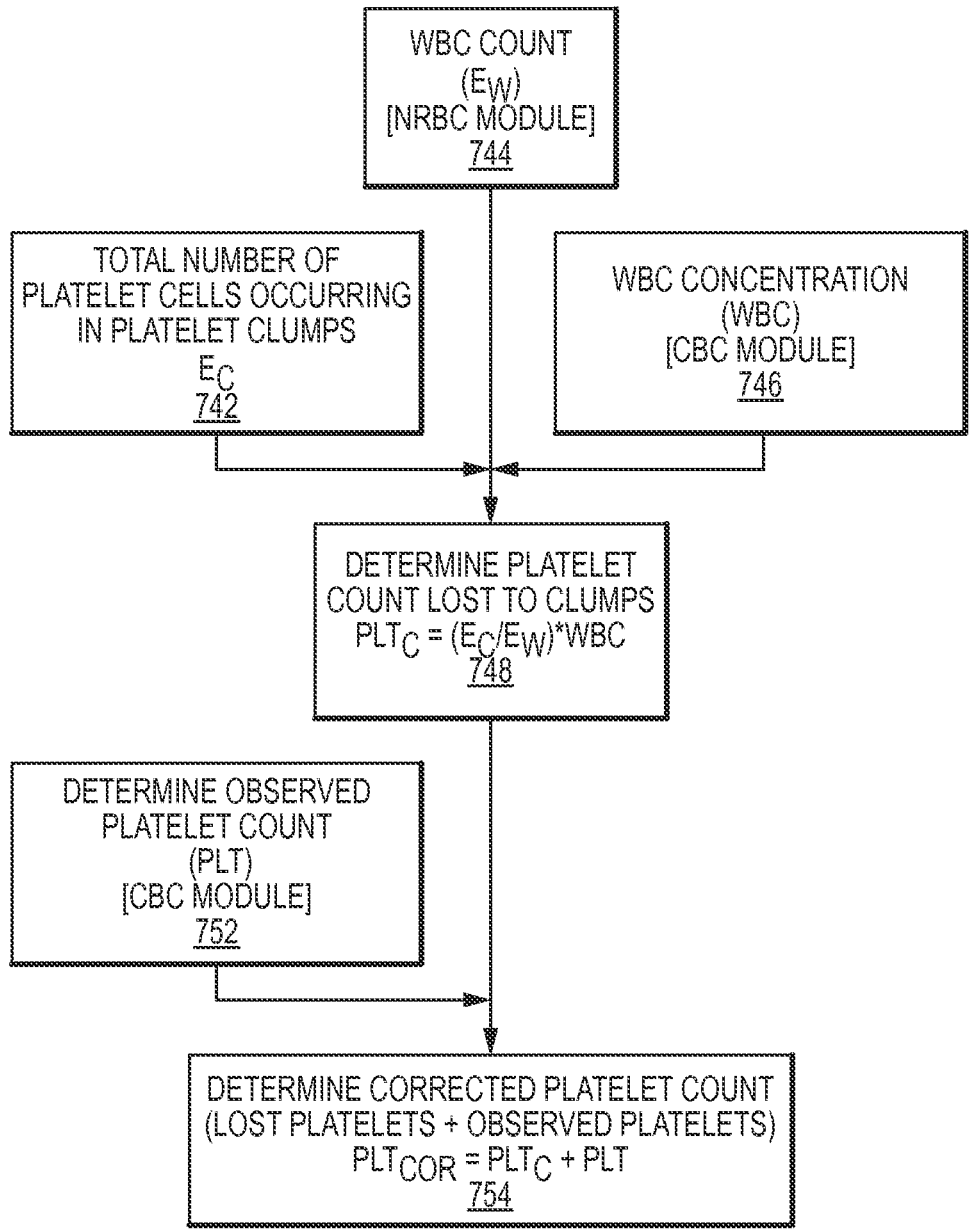

FIGS. 7H to 7J illustrate aspects of an exemplary method for determining a corrected platelet count, according to embodiments of the present invention. As shown in FIG. 7H, the method may involve establishing a relationship between a CBC module platelet histogram 702 and an NRBC DC histogram 704, for example by processing latex beads of known volume or characteristics 706 through CBC and NRBC modules, respectively. As shown here, a channel in the CBC platelet histogram (e.g. in femtoliter units) can be mapped to a DC channel in the NRBC module, so as to determine a correlation that can be used to transform CBC platelet output to NRBC DC output, as indicated by step 710.

A sample of single platelets 712 having a population size distribution can be processed with a CBC module, as indicated by step 714, to obtain CBC module output corresponding to the single platelet population. Using the correlation obtained in step 710, it is possible to map the CBC module output obtained by step 714 to an NRBC DC space, as indicated by step 716. The transformed NRBC output obtained by step 716 can be normalized, as indicated by step 718, and represented as a probability distribution function of DC measurements for single platelet cells, as illustrated in graph 720.

As shown in FIG. 7I, a sample of clumped platelets 722 having a population size distribution can be processed with an NRBC module, as indicated by step 724, to obtain NRBC module output corresponding to the population of platelet clumps. The biological sample may contain a population of platelet clumps, such that smaller clumps contain fewer numbers of platelets (e.g. n=2), and larger clumps contain greater numbers of platelets (e.g. n=13). In some instances, the platelet clumps present in the sample present a population distribution, such that different clumps include different numbers of platelets. For example, some clumps of the population may include 5 platelets, some clumps may include 10 platelets, some clumps may include 20 platelets, and so on. As shown in step 724, the total number of platelet clump events can be represented as i. Graph 726 illustrates an exemplary NRBC DC histogram, where the DC measurement is represented as $x_i$. For each clump event identified in the NRBC module (e.g. via step 724), it is possible to estimate the number of platelet cells occurring in that clump, using a maximum likelihood approach, as indicated by step 730.

As depicted in graph 720, after normalization, the resulting histogram can be denoted as $p_1(x)$ (where x is DC channel number), thus representing the probability distribution function of the DC measurements of single platelet cells. That probability distribution function $p_1(x)$ can be convolved, as indicated in step 728, to obtain a probability distribution function of DC measurements for platelet clumps containing multiple platelet cells. More specifically, it is possible to calculate the probability distribution functions of the DC measurements for platelet clumps containing multiple platelet cells. The probability distribution function of the DC measurements for platelet clumps containing two platelet cells can be denoted by $p_2(x)$, which is equal to the convolution of $p_1(x)$ and $p_1(x)$. The probability distribution function of the DC measurements for platelet clumps containing n platelet cells is denoted by $p_n(x)$, which is equal to the convolution of $p_{n-1}(x)$ and $p_1(x)$.

As shown in step 730, for each platelet clump event (i) identified in the NRBC module, it is possible calculate the number of platelet cells in the cluster with maximum-likelihood approach based on the probability distribution function of the DC measurements for platelet clumps containing n platelet cells. To be more specific, the estimated number of platelet cells in platelet clump event i (with DC measurement $x_i$) can be determined with the following equation:

$$N_i \cdot N_i = \underset{n}{\mathrm{argmax}} \ [p_n(x_i)]$$

In this way, probability theory can be used to determine the most likely number of the platelets in a clump, for each clump size in a population of platelet clumps. For example, for each observed volume (e.g. platelet clump having a known volume) in a distribution of volumes, it is possible to estimate the number of platelets in that volume (e.g. using the most likely number of platelets per unit volume of clump). As shown in step 732, it is possible to sum the entire clump size range to get the total number of platelets occurring in platelet clumps. As shown here, the total number can be calculated using the following equation:

$$E_c = \sum_i N_i$$

As depicted in FIG. 7J, knowing the total number of platelet cells occurring in platelet clumps ($E_C$) 742 obtained in step 732, the WBC count ($E_W$) 744 obtained from an NRBC module, and the WBC Concentration (WBC) 746 obtained from a CBC module, it is possible to estimate or calculate the platelet count lost to the platelet clumps, as indicated in step 748. For example, the platelet count lost to platelet clumps can be represented as $PLT_c$, and calculated as $PLT_c=(E_c/E_W)*WBC$, where $E_W$ is the number of events of white blood cells in the NRBC module and WBC is the white blood cell concentration from the CBC module.

An observed platelet count (PLT) can be determined by a CBC module as indicated in step 752, and a corrected platelet count can be determined based on the lost platelet count and the observed platelet count as indicated in step 754. For example, the corrected platelet count can be represented as $PLT_{cor}$, and calculated as $PLT_{cor}=PLT_c+PLT$.

Figure 8:
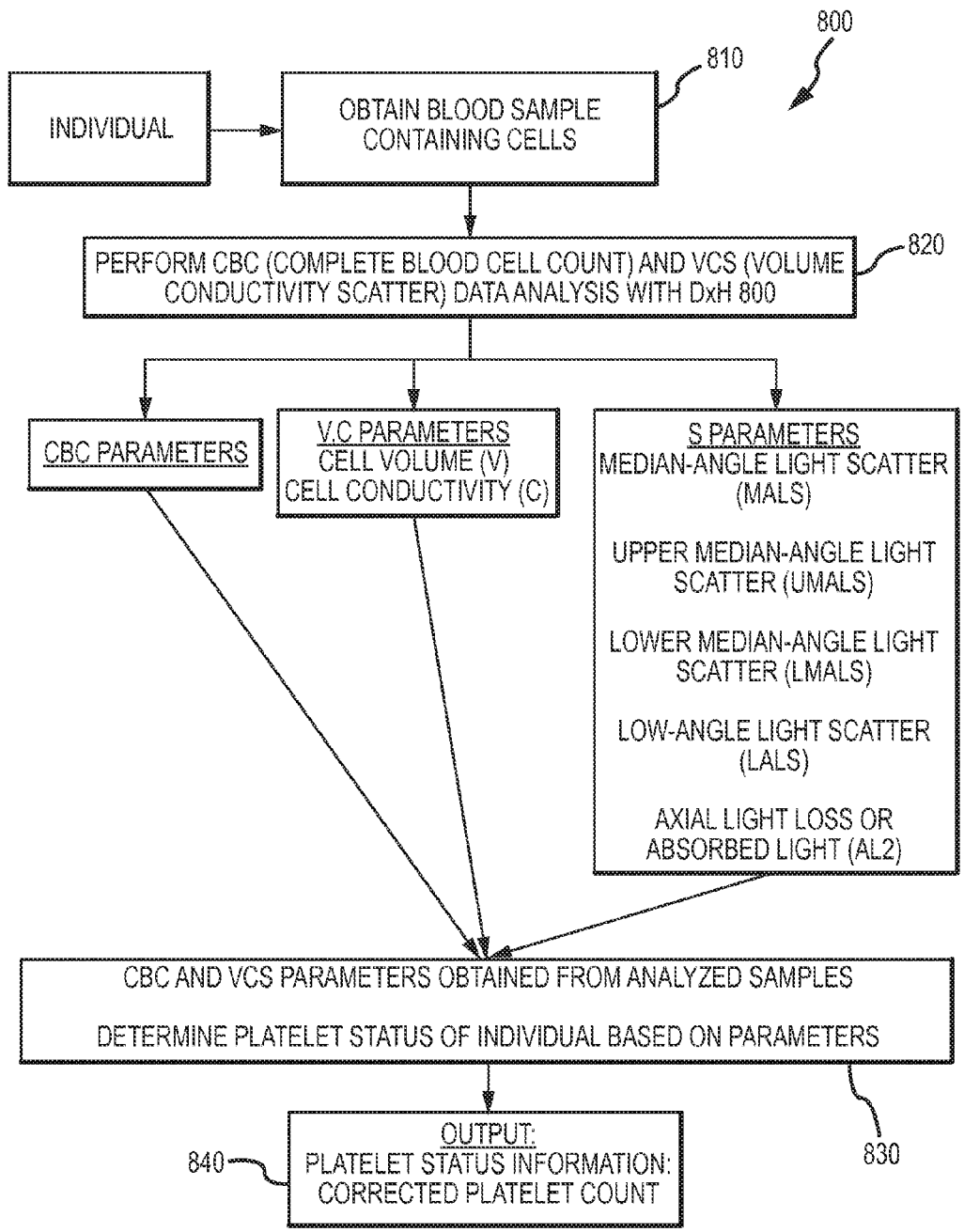
FIG. 8 illustrates aspects of a method for determining platelet status information based on a biological sample obtained from an individual, according to embodiments of the present invention.

FIG. 8 schematically illustrates a method 800 for obtaining a platelet parameter (e.g. corrected platelet count) according to embodiments of the present invention. As depicted here, the method includes obtaining blood samples from individuals (e.g. during routine examinations), as indicated by step 810. Complete Blood Count (CBC) data, Volume Conductivity Scatter (VCS) data, or combinations thereof, can be obtained from these biological samples, using a cellular analysis system that is equipped to obtain cellular event parameters, such as a hematology analyzer, as indicated by step 820. CBC parameters, VCS parameters, or combinations thereof from analyzed samples can be used to determine the platelet parameters, as indicated by step 830. Methods may also include outputting platelet status information, as indicated in step 840.

Analysis Systems

Embodiments of the present invention encompass cellular analysis systems and other automated biological investigation devices which are programmed to carry out platelet status prediction or identification methods according to techniques as disclosed herein. For example, a system that is equipped to obtain and/or process multiple light angle detection parameters, such as a hematology analyzer, or processors or other computer or module systems associated therewith or incorporated therein, can be configured to receive as input values for the various measurements or parameters discussed herein, and automatically output a predicted platelet status. The predicted status may provide an indication that the individual has a normal platelet level, an elevated platelet level, or a depressed platelet level, for example. In some instances, a system that is equipped to obtain and/or process multiple light angle detection parameters, such as a hematology analyzer, may include a processor or storage medium that is configured to automatically implement a platelet analysis, whereby data obtained from a biological sample analyzed by a system that is equipped to obtain multiple light angle detection parameters, such as a hematology analyzer, is also processed by a system that is equipped to obtain and/or process multiple light angle detection parameters, such as a hematology analyzer, and a platelet prediction or indication is provided or output by the system that is equipped to obtain and/or process multiple light angle detection parameters, such as a hematology analyzer, based on the analyzed data.

Figure 9:
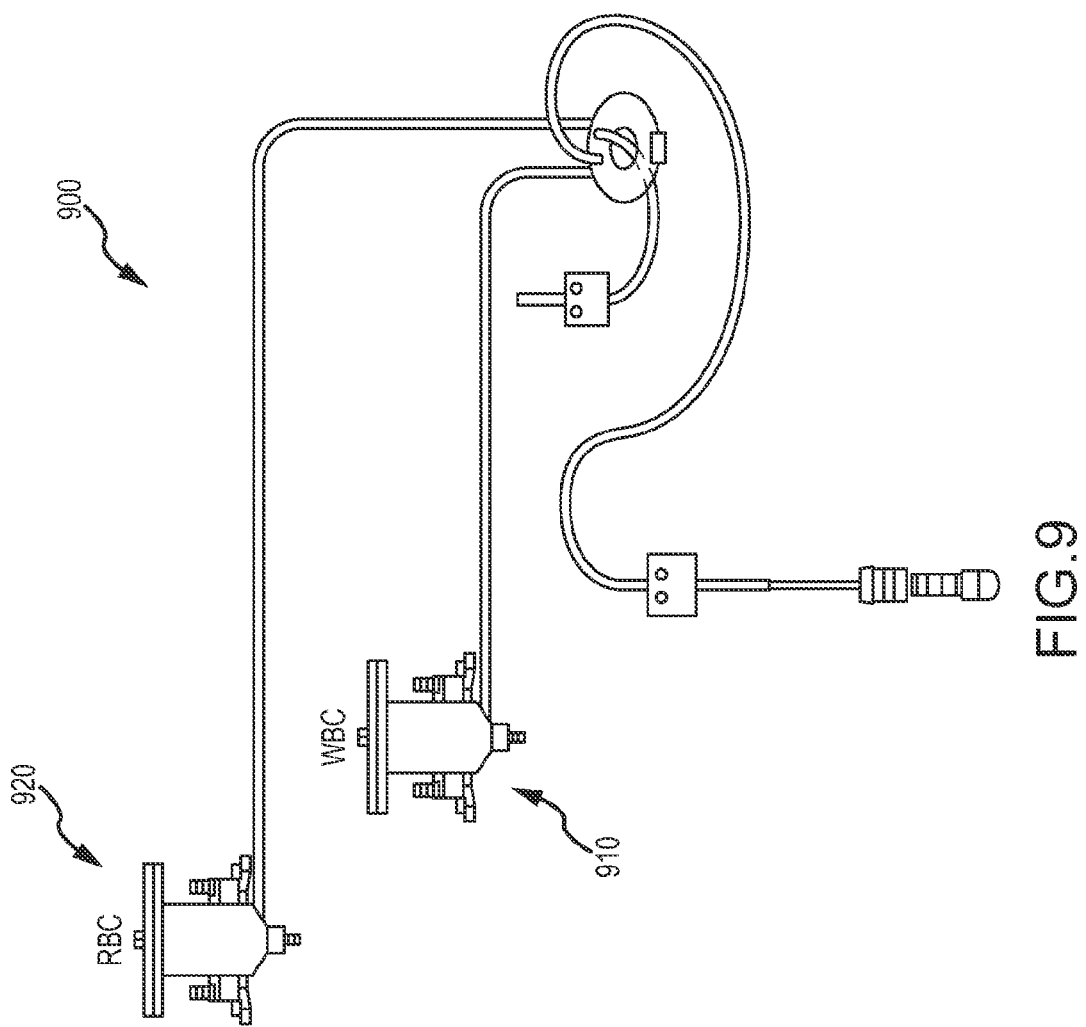
FIGS. 9, 10A, and 10B show aspects of blood cell analysis systems and methods according to embodiments of the present invention.

FIG. 9 depicts aspects of an exemplary CBC module 900, according to embodiments of the present invention. Such CBC modules, which may be part of a system such as a hematology analyzer, can operate to control or carry out various mechanical functions as well as electronic and photometric measurement functions for WBC, RBC and PLT cell counting or evaluation and hemoglobin measurements. Exemplary CBC module can be used to prepare the samples for CBC analysis, and to generate CBC parameter measurements via aperture bath assemblies (e.g. WBC bath 910 and RBC bath 920).

Cellular elements of the blood (e.g. erythrocytes, leukocytes, and platelets) can be counted using electrical impedance methods. For example, an aspirated whole blood sample can be divided into two aliquots and mixed with an isotonic diluent. The first dilution can be delivered to the RBC aperture bath 920, and the second can be delivered to the WBC aperture bath 910. In the RBC chamber, both RBCs and platelets can be counted and discriminated by electrical impedance as the cells pass through sensing apertures. For example, particles between 2 and 20 fL can be counted as platelets, and those greater than 36 fL can be counted as RBCs. For the WBC chamber processing, an RBC-lysing reagent can be added to the WBC dilution aliquot to lyse RBCs and release hemoglobin, and then WBCs can be counted by impedance in sensing apertures of the WBC bath. In some instances, the baths may include multiple apertures. Hence, for example, a platelet event count used in a platelet enumeration technique may be obtained using an RBC triple aperture bath. Similarly, a WBC event analysis (such as WBC concentration) used in a platelet enumeration technique may be obtained using a WBC triple aperture bath.

An exemplary CBC sample preparation technique may include two processes, sample acquisition and sample delivery. Sample acquisition may occur when 165 uL of patient sample is aspirated and directed to a Blood Sampling Valve (BSV), for example as depicted in FIG. 7G. The BSV can operate to direct specific volumes of the patient sample with the hematology analyzer reagents for delivery to the two triple-aperture baths. The patient sample and the hematology analyzer reagents can be delivered to the bottom of aperture baths at an angle that, with a round design, allow the sample and reagents to thoroughly mix without mixing bubbles. The sample can then be prepared for measurement and analysis. According to some embodiments, in the WBC bath, 6.0 mL (±1.0%) of hematology analyzer diluent and 28 uL of sample can be combined with 1.08 mL (±1.0%) of hematology analyzer cell lyse for a final dilution of 1:251. According to some embodiments, in the RBC bath, 10 mL (±1.0%) of hematology analyzer diluent and 1.6 uL of sample can be combined for a final dilution of 1:6250. After the patient sample and hematology analyzer reagents are mixed, vacuum and aperture current can be applied to the apertures for the measurements of cell count and cell volume. The RBC and PLT counts can also include the application of sweep flow to prevent recirculation of cells near the aperture. In certain embodiments, data acquisition for the RBC and PLT can be up to a maximum of 20 seconds and for the WBC a maximum of 10 seconds. In certain embodiments, all analog pulses generated by the aperture assemblies can be amplified by a preamp card and then sent to a CBC signal conditioner analyzer card for analog-to-digital conversion and parameter extraction. According to some embodiments, a system such as a hematology analyzer can be used to measure multiple parameters for each cellular event, and a digital parameter extraction process can be used to provide digital measurements such as time, volume (pulse attributes including amplitude and pulse width), count and count rate, and wait time. Such measurements can be used, optionally by a system such as a hematology analyzer, for pulse editing, coincidence correction, count voting, generation of histograms for WBC, RBC and PLT, histogram voting, pattern analysis, and interference correction, and the like.

Figure 10A:
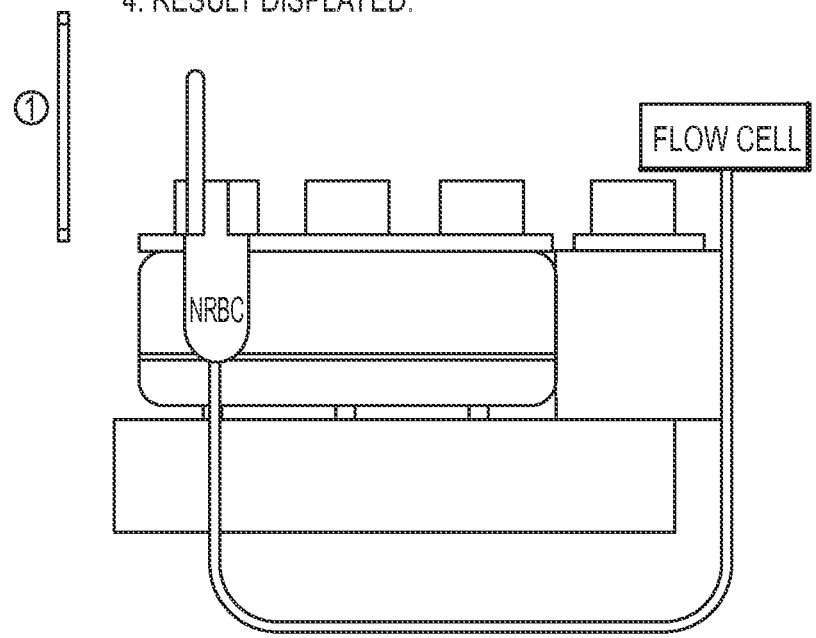
Figure 10B:
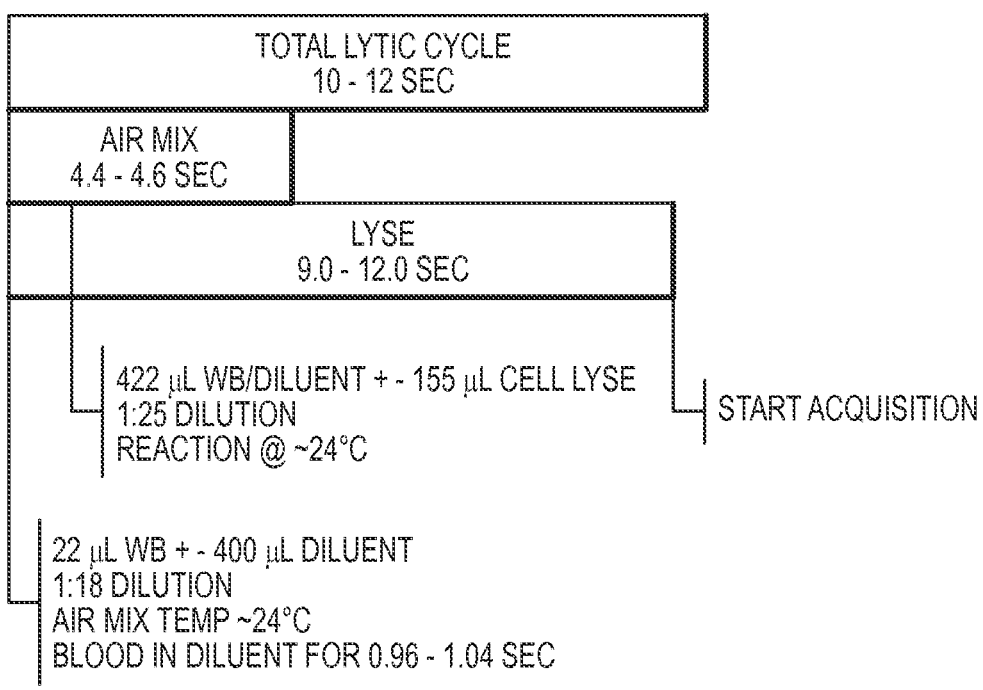

FIG. 10A depicts aspects of an exemplary NRBC processing chamber, according to embodiments of the present invention. Relatedly, FIG. 10B depicts aspects of an exemplary NRBC processing cycle, according to embodiments of the present invention. As shown here, a portion of the blood sample can be diluted and treated with a lysing reagent to selectively remove non-nucleated red blood cells while maintaining NRBCs, WBCs and any platelets or cellular debris that may be present in predictable state. An exemplary NRBC analysis protocol may include delivering blood to the NRBC chamber, contacting the amount of blood with a cell lysing agent (e.g. by mixing the blood and lysing agent), transporting the mixture to a flow cell for analysis, and displaying the results.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

All patents, patent publications, patent applications, journal articles, books, technical references, and the like discussed in the instant disclosure are incorporated herein by reference in their entirety for all purposes.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A hematology system for determining a platelet status in a biological sample, the system comprising:
    a first module configured to determine a platelet clump event and a white blood cell event;
    a second module configured to determine an observed platelet count and a white blood cell concentration; and
    a data processing module in connectivity with the first module and the second module, wherein the data processing module comprises a processor and a tangible non-transitory computer readable medium, the computer readable medium programmed with a computer application that, when executed by the processor, causes the processor to determine the platelet status based on the sum of the observed platelet count and a lost platelet count, wherein the lost platelet count comprises a multiplication product of a first factor and a second factor, the first factor based on the platelet clump event and the white blood cell event, and the second factor comprising the white blood cell concentration.

2. The system according to claim 1, wherein the first module is a volume conductivity scatter (VCS) module.

3. The system according to claim 1, wherein the second module is a complete blood count (CBC) module.

4. The system according to claim 1, wherein the platelet status comprises an estimated corrected platelet count.

5. The system according to claim 1, wherein the first module comprises:
    an optical element having a cell interrogation zone;
    a flow path configured to deliver a hydrodynamically focused stream of the biological sample toward the cell interrogation zone;
    an electrode assembly configured to measure direct current (DC) impedance of cells of the biological sample passing individually through the cell interrogation zone;
    a light source oriented to direct a light beam along a beam axis to irradiate the cells of the biological sample individually passing through the cell interrogation zone;
    a light detection assembly optically coupled to the cell interrogation zone so as to measure light scattered by and transmitted through the irradiated cells of the biological sample, the light detection assembly configured to measure:
        a first propagated light from the irradiated cells within a first range of relative to the light beam axis;
        a second propagated light from the irradiated cells within a second range of angles relative to the light beam axis, the second range being different than the first range; and
        an axial light propagated from the irradiated cells along the beam axis.

6. The system according to claim 1, wherein the second module comprises:
    a first aperture bath configured to determine the observed platelet count; and
    a second aperture bath configured to determine the white blood cell concentration.

7. The system according to claim 6, wherein the first aperture bath comprises a red blood cell aperture bath and the second aperture bath comprises a white blood cell aperture bath.

8. The system according to claim 1, wherein the first module is a nucleated red blood cell module.

9. The system according to claim 1, wherein the biological sample comprises a blood sample of an individual.

10. The system according to claim 1, wherein the lost platelet count comprises a multiplication product of the first factor, the second factor, and a third factor, and wherein the first module is configured to determine a platelet clump volume and the second module is configured to determine a single platelet volume, the third factor comprising a ratio of the platelet clump volume to the single platelet volume, and the first factor comprising a ratio of the platelet clump event to the white blood cell event.

11. The system according to claim 10, wherein the first module is configured to determine the platelet clump event based on a light measurement comprising a member selected from the group consisting of a rotated lower angle light scatter (RLALS) measurement, an extended lower median angle light scatter (ELMALS) measurement, a rotated upper median angle light scatter (RUMALS) measurement, and an axial light loss (ALL) measurement.

12. The system according to claim 1, wherein the computer application of the data processing module, when executed by the processor, causes the processor to determine a respective number of platelet cells for each platelet clump event based on a probability distribution function and to determine a total number of platelet cells occurring in platelet clumps based on a sum of the respective numbers of platelet cells for each platelet clump, and wherein the first factor comprises a ratio of the total number of platelet cells occurring in platelet clumps to the white blood cell event.

13. The system according to claim 12, wherein the respective number of platelet cells for each platelet clump event is based on a maximum-likelihood estimation.

14. The system according to claim 12, wherein the first module is configured to determine the platelet clump event based on current (DC) impedance measurement.

15. An automated method for determining a platelet status in a biological sample, the method comprising:
    determining, using a first module, a platelet clump event and a white blood cell event;

determining, using a second module, an observed platelet count and a white blood cell concentration; and determining, using a data processing module, the platelet status based on the sum of the observed platelet count and a lost platelet count, wherein the lost platelet count comprises a multiplication product of a first factor and a second factor, the first factor based on the platelet clump event and the white blood cell event, and the second factor comprising the white blood cell concentration, further wherein the data processing module comprises a processor and a tangible non-transitory computer readable medium that is programmed with a computer application that, when executed by the processor, causes the processor to determine the platelet status.

16. The method according to claim 15, wherein the first module is a volume conductivity scatter (VCS) module.

17. The method according to claim 15, wherein the second module is a complete blood count (CBC) module.

18. The method according to claim 15, wherein the platelet status comprises an estimated corrected platelet count.

19. The method according to claim 15, wherein determining the platelet clump event and the white blood cell event using the first module comprises:
- delivering a hydrodynamically focused stream of the biological sample toward a cell interrogation zone of an optical element;
- measuring, with an electrode assembly, current (DC) impedance of cells of the biological sample passing individually through the cell interrogation zone;
- irradiating, with an electromagnetic beam having an axis, cells of the biological sample individually passing through the cell interrogation zone;
- measuring, with a light detection assembly, a first propagated light from the irradiated cells within a first range of relative to the beam axis;
- measuring, with the light detection assembly, a second propagated light from the irradiated cells within a second range of angles relative to the beam axis, the second range being different than the first range; and
- measuring, with the light detection assembly, axial light propagated from the irradiated cells along the beam axis.

20. The method according to claim 15, wherein determining the observed platelet count and the white blood cell concentration using the second module comprises analyzing the biological sample with a first aperture bath configured to determine the observed platelet count, and with a second aperture bath configured to determine the white blood cell concentration.

21. The method according to claim 20, wherein the first aperture bath comprises a red blood cell aperture bath and the second aperture bath comprises a white blood cell aperture bath.

22. The method according to claim 15, wherein the first module is a nucleated red blood cell module.

23. The method according to claim 15, wherein the biological sample comprises a blood sample of an individual.

24. The method according to claim 15, further comprising determining a platelet clump volume using the first module and a single platelet volume using the second module, wherein the lost platelet count comprises a multiplication product of the first factor, the second factor, and a third factor, the third factor comprising a ratio of the platelet clump volume to the single platelet volume, and the first factor comprising a ratio of the platelet clump event to the white blood cell event.

25. The method according to claim 23, wherein the first module determines the platelet clump event based on a light measurement comprising a member selected from the group consisting of a rotated lower angle light scatter (RLALS) measurement, an extended lower median angle light scatter (ELMALS) measurement, a rotated upper median angle light scatter (RUMALS) measurement, and an axial light loss (ALL) measurement.

26. The method according to claim 15, wherein the computer application of the data processing module, when executed by the processor, causes the processor to determine a respective number of platelet cells for each platelet clump event based on a probability distribution function and determine a total number of platelet cells occurring in platelet clumps based on a sum of the respective numbers of platelet cells for each platelet clump, and wherein the first factor comprises a ratio of the total number of platelet cells occurring in platelet clumps to the white blood cell event.

27. The method according to claim 26, wherein the computer application of the data processing module, when executed by the processor, causes the processor to determine the respective number of platelet cells for each platelet clump event is based on a maximum-likelihood estimation.

28. The method according to claim 26, wherein the first module determines the platelet clump event based on current (DC) impedance measurement.

\* \* \* \* \*